United States Patent [19]
Tanabe et al.

[11] Patent Number: 5,994,413
[45] Date of Patent: *Nov. 30, 1999

[54] PROCESS FOR THE PRODUCTION OF FRUIT POLYPHENOLS FROM UNRIPE ROSACEAE FRUIT

[75] Inventors: Masayuki Tanabe, Matsudo; Tomomasa Kanda, Kashiwa; Akio Yanagida, Tokyo, all of Japan

[73] Assignee: The Nikka Whisky Distilling Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/784,546

[22] Filed: Jan. 21, 1997

Related U.S. Application Data

[63] Continuation of application No. 08/278,080, Jul. 20, 1994, abandoned.

[30] Foreign Application Priority Data

Dec. 6, 1993 [JP] Japan ................................. 5-305632
Feb. 22, 1994 [JP] Japan ................................. 6-024435

[51] Int. Cl.⁶ .................................................. A01N 31/08
[52] U.S. Cl. ......................... 514/732; 514/734; 514/738; 424/195.1
[58] Field of Search .................................. 514/732, 731, 514/738; 424/195.1

[56] References Cited

U.S. PATENT DOCUMENTS

| | | |
|---|---|---|
| 4,258,037 | 3/1981 | Juvin . |
| 4,601,905 | 7/1986 | Széles . |
| 4,910,182 | 3/1990 | Hums et al. ............................ 502/402 |
| 5,141,611 | 8/1992 | Ford .................................... 204/182.4 |

FOREIGN PATENT DOCUMENTS

| | | |
|---|---|---|
| 27 46 950 | 6/1978 | Germany . |
| 32 09 419 | 9/1982 | Germany . |
| WO 88/09178 | 12/1988 | WIPO . |

OTHER PUBLICATIONS

Vigorov, L. I., "Catechins in Apples", Fenol'nye Soedin. Ikh Biol. Funks., Mater. Vses. Simp., 1st (1968), vol. 202–8, pp. 1–10 of translation, Dec. 1968.
Database CAPLUS on STN, No. 1983:469116, Matsuo et al., "Application of high porous polymer to horticultural products. I. Adsorption and elution of polyphenolic compounds.", (Fac. Agric., Kagoshima Univ., Kagoshima, Japan), Kagoshima Daigaku Nogakubu Gaku 1983.
Vigorov, L. I., "Catechins in Apples", Fenol'nye Soedin. Ikh Biol. Funks., Mater. Vses. Simp., 1st (1968), vol. 202–8, (abstract only).
Terao et al., "Protective Effect of Epicatechin, Epicatechin Gallate, and Quercetin on Lipid Peroxidation in Phospholipid Bilayers", Archives of Biochemistry and Biophysics, vol. 308, No. 1, pp. 278–284 (Jan., 1994).

Sakanaka et al., "Inhibitory Effects of Green Tea Polyphenols on Glucan Synthesis and Cellular Adherence of Cariogenic Streptococci", Agric. Biol. Chem,, 54(II), pp. 2925–2929 1990.
Vigorov, L. I., "Catechins in Apples", Fenol'nye Soedin. Ikh Biol. Funks,. Mater. Vses. Simp., 1st (1968), vol. 202–8, (abstract only).
Kakegawa et al., "Inhibitory effects of some natural products on the activation of Hyaluronidase and Their Anti–allergic Actions", Chem. Pharm. Bull. 49(6), pp. 1439–1442 (Jun. 1992).
Liquid Chromatographic Determination of Apple Pulp Procyanidins—F. F. Perez–Ilzarbe et al, Journal of Liquid Chromatography, 15(4) pp. 637–646 (1992).
Protective Effect of Epicatechin, Epicatechin Gallate, and Quercetin on Lipid Peroxidation in Phospholidip Bilayers— Junki Terao et al, Archives of Biochemistry and Biophysics, vol. 308, No. 1, pp.278–284 (Jan., 1994).
Inhibitory Effects of Condensed Tannins on Angiotensin Converting Enzyme—Shinji Uchida et al, Short Communication, J. Pharmacol 43, pp. 242–246, (Japan, 1987).
Antihypertensive Substance in Seeds of Areca Catechu L.—Jin–ichi Inokuchi et al, Life Sciences, vol. 38, pp. 1375–1382 (Feb. 6, 1986).
Inhibitory Effects of Green Tea Polyphenols on Glucan Synthesis and Cellular Adherence of Cariogenic Streptococci—Senji Sakanaka et al, Agric. Biol. Chem., 54(II), pp. 2925–2929 (1990).
Preventive Effect of Green Tea Polyphenols Against Dental Caries in Conventional Rats—Senji Sakanaka et al, Biosci. Biotech. Biochem. 56(4), pp. 592–594, (1992).
Inhibitory Effect of Oolong Tea Polyphenols on Glucosyltransferases of Mutans Streptococci—Koichi Nakahara et al, Applied and Environmental Microbiology, pp. 968–973 (Apr. 1993).
Antimutagenic Activity of Green Tea Polyphenols—Zhi Y. Wang et al, Mutation Research, 223, pp. 273–285 (1989).
Antimutagenicity of Dialyzates of Vegetables and Fruits— Kazuki Shinohara et al, Agric. Biol. Chem. 52(6), pp. 1369–1375 (1988).
Inhibitory Effect of Tannins on Direct–Acting Mutagens— Takuo Okuda et al, CHem. Pharm. Bull. 32(9) pp. 3755–3758 (1984).
Inhibitory Effects of Some Natural Products on the Activation of Hyaluronidase and their Anti–Allergic Actions— Hisao Kakegawa et al, Chem. Pharm. Bull. 49(6) pp. 1439–1442 (Jun. 1992).

*Primary Examiner*—Dwayne C. Jones
*Attorney, Agent, or Firm*—Armstrong, Westerman, Hattori, McLeland & Naughton

[57] ABSTRACT

The present invention provides a fruit polyphenol obtained by subjecting unripe fruits of Rosaceae to pressing and/or extraction and then purifying the resulting juice or extract. The present invention further provides an antioxidant, a hypotensive agent, an antimutagenic agent, an antiallergic agent and an anticariogenic agent each comprising, as an effective component, a fruit polyphenol obtained by subjecting unripe fruits of Rosaceae to pressing and/or extraction and then purifying the resulting juice or extract. The fruit polyphenol of the present invention has various physiological activities, for example, an antioxidative activity, an ACE-inhibiting activity, an antimutagenic activity, a hyalulonidase-inhibiting activity and a GTase-inhibiting activity.

7 Claims, 18 Drawing Sheets n = 7 ~ 10

PROCESS FOR THE PRODUCTION OF FRUIT POLYPHENOLS FROM UNRIPE ROSACEAE FRUIT

This application is a continuation of application Ser. No. 08/278,080 filed Jul. 20, 1994, now abandoned.

BACKGROUND OF THE INVENTION AND THE RELATED ART

The present invention relates to a fruit polyphenol; a process for production thereof; and an antioxidant, a hypotensive agent, an antimutagenic agent, an antiallergic agent and an anticariogenic agent each comprising said polyphenol as an effective component.

In growing the trees of Rosaceae which bear edible fruits such as apple, pear, peach and the like, "thinning-out" of superfluous fruits is generally carried out in the period of mid May to mid July. In this thinning-out, unripe fruits in the form of bunch or cluster are removed with some of them left unremoved. Consequently, a large amount of unripe fruits are disposed by the thinning-out, without being utilized. These unripe fruits are very bitter as compared with ripe fruits, and the sectional surface of each unripe fruit turns brown easily. This fact suggests the presence of a large amount of polyphenol compounds in unripe fruits.

It is known that polyphenol compounds are generally present in the plant kingdom as a secondary metabolite of plant in numerous kinds and in a large amount. Some of these polyphenol compounds have drawn attention for their diversified physiological activities, from the past in the field of pharmacology and in recent years in the field of food chemistry.

Among them, tea polyphenol (catechins) is drawing particular attention and concentrated researches are under way thereon. This tea polyphenol is being recognized to have very wide physiological activities such as antibacterial activity, antiviral activity, antioxidative activity, antimutagenic activity, anticancerous activity, platelet coagulation-inhibiting activity, blood pressure increase-inhibiting activity, blood sugar increase-inhibiting activity, blood cholesterol-reducing activity, anticariogenic activity, anti-allergic activity, intestinal flora-improving activity, deodoring activity and the like [Japanese Patent Application Kokai (Laid-Open) Nos. 214183/1988, 6499/1990, 178320/1992, etc.].

Thus, it is known that, for example, the polyphenol extracted from tea has wide physiological activities.

SUMMARY OF THE INVENTION

An object of the present invention is to provide a fruit polyphenol having various physiological activities, which is different from the polyphenol extracted from tea.

Another object of the present invention is to provide a process for producing the above fruit polyphenol effectively and economically.

According to the present invention, there is provided a fruit polyphenol obtained by subjecting unripe fruits of Rosaceae, particularly unripe apples, unripe pears or unripe peaches to pressing and/or extraction and then purifying the resulting juice or extract.

According to the present invention, there is further provided a process for producing a fruit polyphenol, which comprises subjecting unripe fruits of Rosaceae, particularly unripe apples, unripe pears or unripe peaches to pressing and/or extraction and then purifying the resulting juice or extract to obtain a polyphenol fraction.

According to the present invention, there is further provided an antioxidant comprising, as an effective component, a fruit polyphenol obtained by subjecting unripe fruits of Rosaceae, particularly unripe apples, unripe pears or unripe peaches to pressing and/or extraction and then purifying the resulting juice or extract.

According to the present invention, there is further provided a hypotensive agent comprising, as an effective component, a fruit polyphenol having an inhibitory activity for angiotensin converting enzyme I, which polyphenol is obtained by subjecting unripe fruits of Rosaceae, particularly unripe apples, unripe pears or unripe peaches to pressing and/or extraction and then purifying the resulting juice or extract.

According to the present invention, there is further provided an antimutagenic agent comprising, as an effective component, a fruit polyphenol having an activity capable of inhibiting the mutagenicity of carcinogenic substance, which polyphenol is obtained by subjecting unripe fruits of Rosaceae, particularly unripe apples, unripe pears or unripe peaches to pressing and/or extraction and then purifying the resulting juice or extract.

According to the present invention, there is further provided an antiallergic agent comprising, as an effective component, a fruit polyphenol having a hyaluronidase-inhibiting activity, which polyphenol is obtained by subjecting unripe fruits of Rosaceae, particularly unripe apples, unripe pears or unripe peaches to pressing and/or extraction and then purifying the resulting juice or extract.

According to the present invention, there is further provided an anticariogenic agent comprising, as an effective component, a fruit polyphenol having a glucosyltransferase-inhibiting activity, which polyphenol is obtained by subjecting unripe fruits of Rosaceae, particularly unripe apples, unripe pears or unripe peaches to pressing and/or extraction and then purifying the resulting juice or extract.

DETAILED DESCRIPTION OF THE INVENTION

Figure 1:
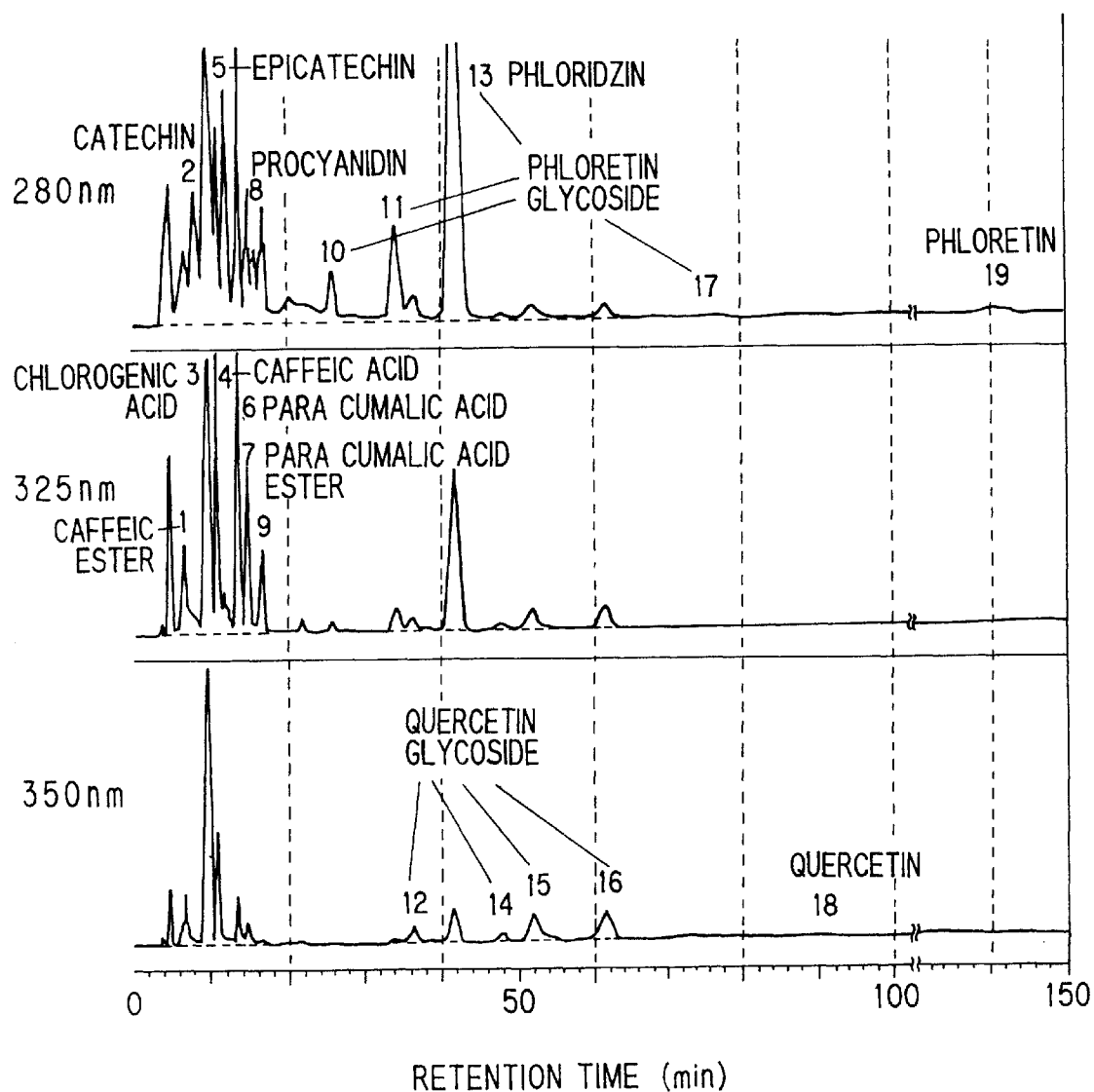
FIG. 1 is graphs showing the HPLC chromatogram and the comparison of UV spectle of each peaks of unripe apple polyphenol.

The fruit polyphenol according to the present invention is a polyphenol obtained by subjecting unripe fruits of Rosaceae, particularly unripe apples, unripe pears or unripe peaches to pressing or extraction and then purifying the resulting juice or extract. The purification is conducted by treating the juice or extract with an adsorbent, and the fraction of the juice or extract adsorbed by the adsorbent (this fraction is hereinafter referred to as "adsorbed fraction") contains a fruit polyphenol. The adsorbed fraction is eluted with an anhydrous alcohol (e.g. ethanol) to obtain a purified polyphenol fraction.

This polyphenol fraction is then concentrated, whereby a liquid polyphenol product can be obtained.

When the concentrate obtained above is subjected to spray-drying or freeze-drying, a powder polyphenol product can be obtained.

The starting material used in the present invention is fruits of Rosaceae. Specifically, apples, pears, peaches, etc. are preferable with apples being particularly preferable. The fruits may be ripe or unripe, but unripe fruits are particularly preferable because they contain polyphenol compounds in a larger total amount and also because they contain various polyphenol compounds having diversified physiological activities, in large amounts.

Description is made on the pressing. In one pressing method, the starting material is washed; the washed material is subjected to crushing and pressing with or without addition of sulfurous acid, to obtain a juice; preferably, a pectolytic enzyme is added thereto; and the resulting mixture is subjected to centrifugation, filtration or the like to obtain a clear juice.

Description is made on the extraction. In one extraction method, the washed material is mixed with an alcohol (e.g. ethanol or methanol); the mixture is subjected to crushing; the resulting material is subjected to extraction while it is being immersed and pressed, or refluxed; the extract is concentrated under reduced pressure to remove the alcohol; and the concentrate is subjected to centrifugation and filtration, or to distribution with an organic solvent (e.g. hexane or chloroform) and filtration, to obtain a clear extract.

Description is made on the purification of the juice or extract obtained above. The clear juice or clear extract obtained above is passed through a column filled with an adsorbent capable of selectively adsorbing the fruit polyphenol contained in the juice or extract and also capable of releasing the adsorbed polyphenol by the use of an elutant, whereby a polyphenol fraction is adsorbed. [Examples of the adsorbent are a styrene-divinylbenzene type synthetic resin, an anion exchange resin and an octadecyl group-chemically bonded silica gel (ODS)]. Then, distilled water is passed through the column for washing. Thereafter, a 20–100% alcohol (e.g. ethanol) solution, preferably an about 50% alcohol solution is passed through the column, whereby a polyphenol fraction is eluted and recovered. The resulting polyphenol solution is concentrated under reduced pressure to remove the alcohol, whereby a fruit polyphenol liquid product (preferably, an organic acid such as malic acid or the like is added therein) can be obtained. This liquid product is subjected to spray-drying or freeze-drying, after addition or no addition of an auxiliary agent for powdering such as dextrin or the like, whereby a fruit polyphenol powder product can be obtained.

According to the confirmation by the present inventor, the fruit polyphenol obtained by the present invention is composed mostly of (1) simple polyphenol compounds such as caffeic acid derivatives, p-coumaric acid derivatives, flavan-3-ols (catechins), flavonols (quercetin glycosides), dihydrochalcones (phloretin glycosides) and the like and (2) high-molecular polyphenol compounds such as condensed tannins and the like.

Thus, the fruit polyphenol obtained in the present invention is considered to have various physiological functions, and the present inventor made an extensive study. As a result, it was first found that the fruit polyphenol of the present invention contains a large amount of a component capable of inhibiting the oxidation of linoleic acid (a vegetable oil). Therefore, the fruit polyphenol of the present invention is very effective as an antioxidant.

It was next found that the fruit polyphenol of the present invention contains a large amount of a component capable of inhibiting the function of ACE (this is an enzyme connected with an increase in blood pressure). Therefore, the fruit polyphenol of the present invention is very effective also as a hypotensive agent.

A further study was made to identify the ACE-inhibiting component contained in the fruit polyphenol of the present invention. As a result, the ACE-inhibiting component was confirmed to be a condensed tannin represented by the structural formula shown in FIG. 12.

Many researches conducted in recent years indicated that there is a high correlation between carcinogenic substance and mutagenic substance and accordingly there is a deep connection between carcinogenicity and mutagenicity. Consequently, a substance capable of inhibiting mutagenicity is expected to be able to prevent carcinogenicity. The present inventor examined whether or not the fruit polyphenol of the present invention has an antimutagenic activity, and confirmed that the polyphenol has said activity. Therefore, the fruit polyphenol of the present invention is very effective also as an antimutagenic agent.

Hyaluronidase is an enzyme which is considered to exhibit a certain cell activity in the reconstruction of connective tissue. Researches conducted in recent years (Chem. Pharm. Bull., 33, p. 642, 1985; ibid., 33, p. 5079, 1985; ibid., 33, p. 3787, 1985; ibid., 33, p. 5079, 1985; and ibid., 40, p. 1439, 1992) indicated that in synthetic antiallergic agents (e.g. sodium cromoglicate and tranilast) there is a high correlation between the hyaluronidase-inhibiting activity and the activity for suppressing the release of histamine from mast cells. Utilizing this correlation, several antiallergic substances were found in natural products by measuring said products for hyaluronidase-inhibiting activity. Hence, the present inventor examined whether or not the fruit polyphenol of the present invention has a hyaluronidase-inhibiting activity, and confirmed that the polyphenol has said activity. Therefore, the fruit polyphenol of the present invention is very effective also as an antiallergic agent.

Dental caries (decayed tooth) is currently confirmed to be a bacteria-related disease caused by oral Streptococcus including *Streptococcus mutans*. In the process of dental caries development, formation of deposit is considered to be a particularly important factor.

That is, there is synthesized, from the sucrose contained in foods, sticky and insoluble glucan by the action of glucosyltransferase (hereinafter referred to as "GTase") which is an enzyme produced by cariogenic bacteria; bacteria adhere on the dentin via said glucan; and the resulting deposit causes dental caries.

Thus, substances capable of inhibiting GTase's action are expected to be effective as an anticariogenic agent [Appl. Env. Microbiol., 59 (4), pp. 968–973, 1993; Biosci. Biotech. Biochem., 56 (5), pp. 766–768, 1992; Agric. Biol. Chem., 54 (11), pp. 2925–2929, 1990; and Chem. Pharm. Bull., 38 (3), pp. 717–720, 1990].

Hence, the present inventor examined whether or not the fruit polyphenol of the present invention has an inhibitory activity to insoluble glucan-producing GTase which is produced by *S. sobrinus* (a typical cariogenic bacteria), and found that the polyphenol has said activity. Therefore, the fruit polyphenol of the present invention is very effective also as an anticariogenic agent.

Next, the present invention is described in more detail referring to Examples. However, the present invention is not restricted to these Examples.

EXAMPLE 1

Compositional analysis of unripe apple juice

The following samples were subjected to general compositional analysis.

Samples

Ripe apple "Fuji": commercial product grown using no bag

Unripe apple "Fuji": collected in mid June

Treatment of samples

Each fruit sample was crushed by means of a mixer, with an appropriate amount of potassium metabisulfite (an antioxidant) being added. The resulting juice was subjected to centrifugation and filtration to obtain a clear juice. Each clear juice was measured for the following items.

Measurement items (and methods)
    x Average weight of individual fruits (n=50)
    x Ratio of juice obtained (%)
    x pH
    x Acidity (g/l in terms of malic acid)
    x Brix
    x Total phenols (ppm in terms of chlorogenic acid)
    x Total ascorbic acid
    x Analysis of organic acids
    x Analysis of saccharide
    x Analysis of metal ions
    x Analysis of free amino acids
The results of measurements are shown in Table 1.

TABLE 1

| | Average weight of individual fruits(g) | Ratio of juice obtained(%) | pH | Acidity(g/l in terms of malic acid) | Brix | Total phenols(ppm in terms of chlorogenic acid) | Total ascorbic acid(ppm) |
|---|---|---|---|---|---|---|---|
| Ripe "Fuji" juice | 287.2 | 66.1 | 3.88 | 2.73 | 11.6 | 720 | — |
| Unripe "Fuji" juice | 5.1 | 51.0 | 3.78 | 6.83 | 5.2 | 6,200 | 254 |

| | Metal ions (ppm) | | | | |
|---|---|---|---|---|---|
| | K | Ca | Mg | Fe | Na |
| Ripe "Fuji" juice | 1,430 | 15 | 16 | 0 | 9 |
| Unripe "Fuji" juice | 3,050 | 250 | 130 | 13 | 28 |

| | Organic acids (%) | | | Saccharide (%) | | | |
|---|---|---|---|---|---|---|---|
| | Malic acid | Quinic acid | (Total) | Glucose | Fructose | Sucrose | Sorbitol | (Total) |
| Ripe "Fuji" juice | 0.39 | 0.02 | (0.41) | 2.12 | 6.72 | 2.52 | 0.31 | (11.67) |
| Unripe "Fuji" juice | 0.49 | 1.17 | (1.65) | 0.70 | 0.49 | 0.03 | 0.44 | (1.66) |

| | Free amino acids | | | | | | | | | | | | | | | | | | | | | | |
|---|---|---|---|---|---|---|---|---|---|---|---|---|---|---|---|---|---|---|---|---|---|---|---|
| | ASP | THR | SER | ASN | GLU | GLN | GLY | ALA | CIT | VAL | MET | ILEU | LEU | TYR | PHE | α-ABA | γ-ABA | MEA | HYLYS | 1M-HIS | HIS | LIS | ARG |
| Ripe "Fuji" juice | 211 | 2 | 10 | 207 | 29 | 2 | 36 | 4 | 3 | 2 | | 7 | 52 | | 114 | | 3 | | | 9 | 14 | 19 | 47 | 34 |
| Unripe "Fuji" juice | 32 | 40 | 42 | 3,280 | | 13 | | 52 | 4 | 37 | 8 | 25 | 76 | | | | 337 | 44 | | | | | |

As is clear from Table 1, there is a big difference in composition between unripe apple juice and ripe apple juice. In the unripe apple juice were abundant, in particular, total phenols, total ascorbic acid, organic acids (particularly, quinic acid), metal ions and free amino acids (asparagine, phenylalanine and γ-aminobutyric acid, in particular). Meanwhile, saccharide was very little in the unripe apple juice.

Next, the polyphenol contained in unripe apple was subjected to compositional analysis by HLPC.

As the polyphenol sample, there was used a purified polyphenol obtained by subjecting an unripe apple extract to solid-phase extraction (see Example 2).

The results of the analysis is shown in FIG. 1.

As is clear from FIG. 1, the sample polyphenol contained in unripe apple were composed mostly of caffeic acid derivatives (chlorogenic acid, etc.), p-coumaric acid derivatives, flavan-3-ols (catechin, epicatechin, etc.), flavanols (quercetin glycosides) and dihydrochalcones (phloretin glycosides, particularly phloridzin). Among them, chlorogenic acid, catechin, epicatechin and phloridzin were contained in large amounts.

EXAMPLE 2

Antioxidative activities of polyphenols in unripe fruits

Starting materials: the following starting materials were used.

Ripe apple: commercial product grown using no bag
Unripe apples: collected in mid June
"Fuji": average weight=4.97 g (n=50)
"Tugaru": average weight=7.80 g (n=50)
"Jonagold": average weight=3.86 g (n=50)
"Hokuto": average weight=3.32 g (n=50)
"Ohrin": average weight=10.34 g (n=50)
Unripe pear: collected in early June
"Hohsui": average weight=8.98 g (n=50)
Unripe peach: collected in early June
"Akatuki": average weight=5.03 g (n=50)

Preparation of samples

Juice samples: the Example 1 procedure was repeated to obtain clear juices.

Extract samples: each extract sample was obtained by homogenizing 400 g of a starting material together with 1% HCl-containing methanol, subjecting the resulting material to extraction (three times) with refluxing, concentrating the extract under reduced pressure to remove methanol, adding chloroform thereto to conduct distribution (two times), recovering the aqueous layer, filtering the aqueous layer, and then adding distilled water to the filtrate to make the total volume 200 ml.

As necessary, the juice samples and the extract samples were subjected to solid-phase extraction using Sep-pack C18 to obtain polyphenol fractions.

Test method for antioxidative activity

The following test method for antioxidative activity was employed.

5 ml of a base solution (ethanol containing 4% of linolic acid) was mixed with 4 ml of a phosphate buffer solution (pH=7.0) and 1 ml of a sample solution in a tightly stoppered test tube. The test tube was kept in a 50° C. thermostat under light shielding. Also kept under the same conditions were a test tube (control) containing ethanol in place of linolic acid and a test tube (blank) containing the sample solvent in place of the sample.

During the storage period, the reaction mixture was sampled with the lapse of time to quantitatively determine the amount of peroxide formed by the isothiocyanate method (the iron rhodanide method).

Results of measurements

Antioxidative activity was examined on the unripe apple "Fuji" extract and the ripe apple "Fuji" extract.

The above two extracts were each added to a reaction system in a concentration range of 1–1,000 μl/g (linolic acid). One weak later the addition, the amount of peroxylipid formed (absorbance at 500 nm) was measured. Its correlation with the concentration of extract added is shown in FIG. 2.

Figure 2:
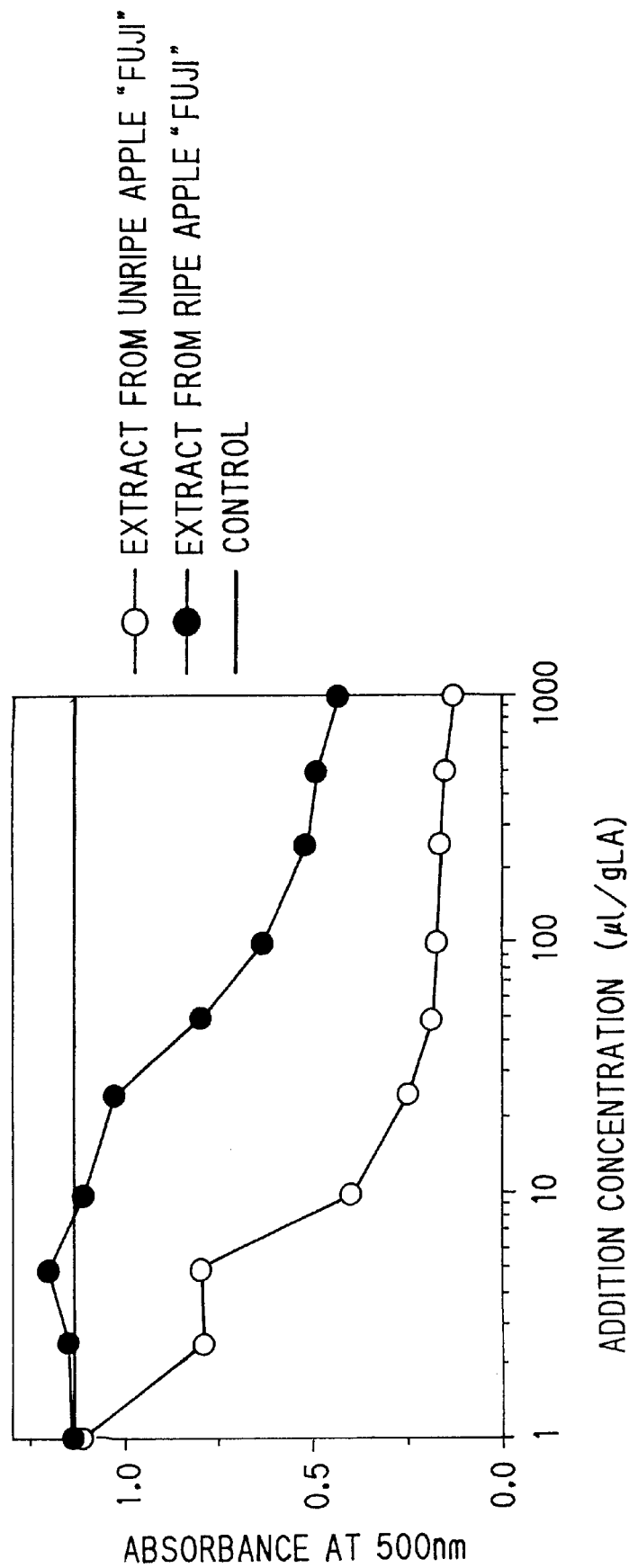
FIG. 2 is graphs each showing the relation between the amount of peroxylipid formed (the absorbance at 500 nm) and the addition concentration of extract from unripe or ripe apple "Fuji", in one week after said extract was added to a reaction system.

As is shown from FIG. 2, the antioxidative activity to linolic acid is seen in both the unripe "Fuji" extract and the ripe "Fuji" extract, but the activity is higher in the unripe "Fuji" extract.

Next, in order to investigate what the substances of antioxidative activity were, the unripe "Fuji" extract and the ripe "Fuji" extract were each largely divided into two fractions, i.e. a fraction A (a non-adsorbed fraction) and a fraction B (an adsorbed fraction, a polyphenol fraction), using Sep-pack C18. Each extract, each fraction A and each fraction B were independently added to a reaction system in a concentration range of 1–1,000 μl/g (linolic acid). One week after the addition, the amount of peroxylipid formed (absorbance at 500 nm) was measured. Its correlation with the amount of extract or fraction A or B is shown in FIG. 3.

Figure 3:
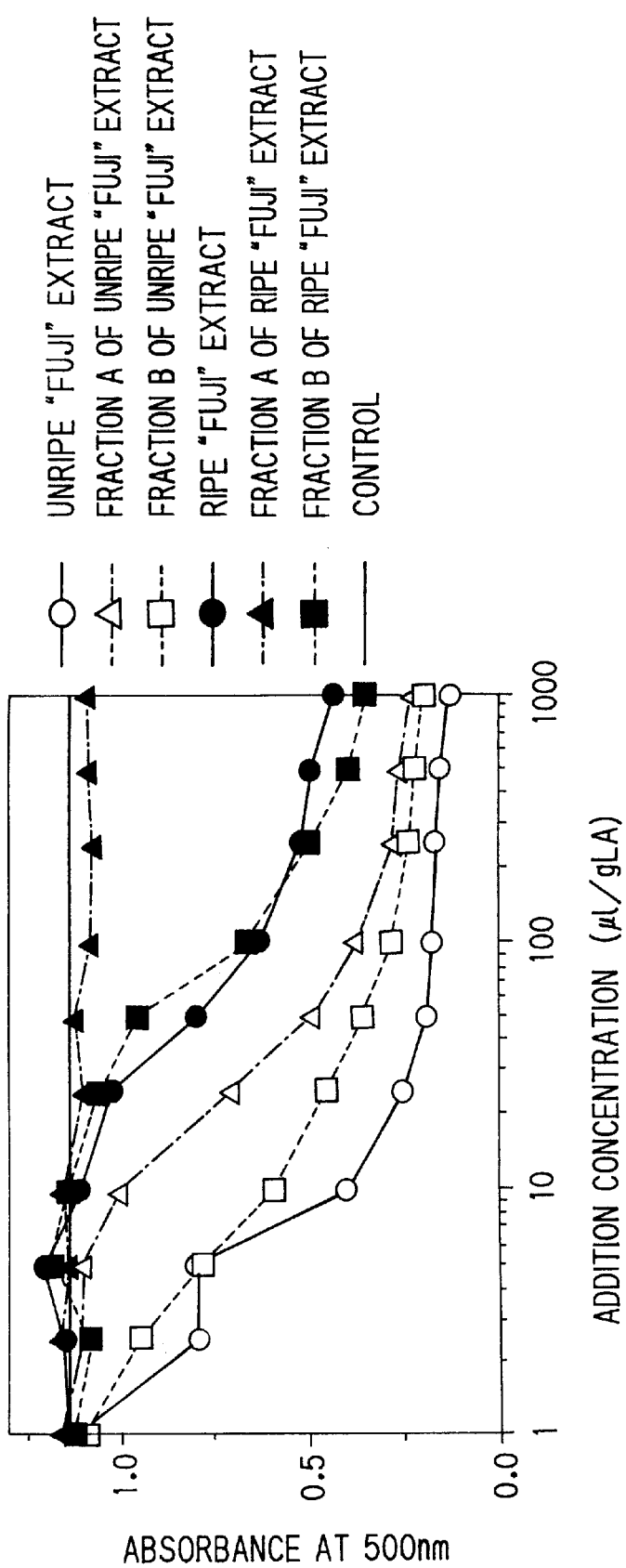
FIG. 3 is graphs each showing the relation between the amount of peroxylipid formed (the absorbance at 500 nm) and the addition concentration of polyphenol fraction of unripe or ripe apple "Fuji", in one week after said fraction was added to a reaction system.

It is clear from FIG. 3 that the antioxidative activity of the ripe apple "Fuji" extract is based on the fraction B of the extract. In the unripe apple "Fuji" extract, both of the fractions A and B have antioxidative activity but the activity of the fraction B is higher.

From the above, it is indicated that the antioxidative activities of the ripe and unripe apple "Fuji" extracts are mostly based on the compounds present in the fractions B, i.e. the polyphenol compounds present in the fractions B.

Of the simple polyphenol compounds contained in apples, those compounds of commercial availability were measured for antioxidative activity. Each of such compounds was added to a reaction system in a concentration of 2 μM/g (linolic acid). One week after the addition, the amount of peroxylipid formed (absorbance at 500 nm) was measured. The absorbances in one week after various polyphenol compounds were added, are shown in FIG. 4.

Figure 4:
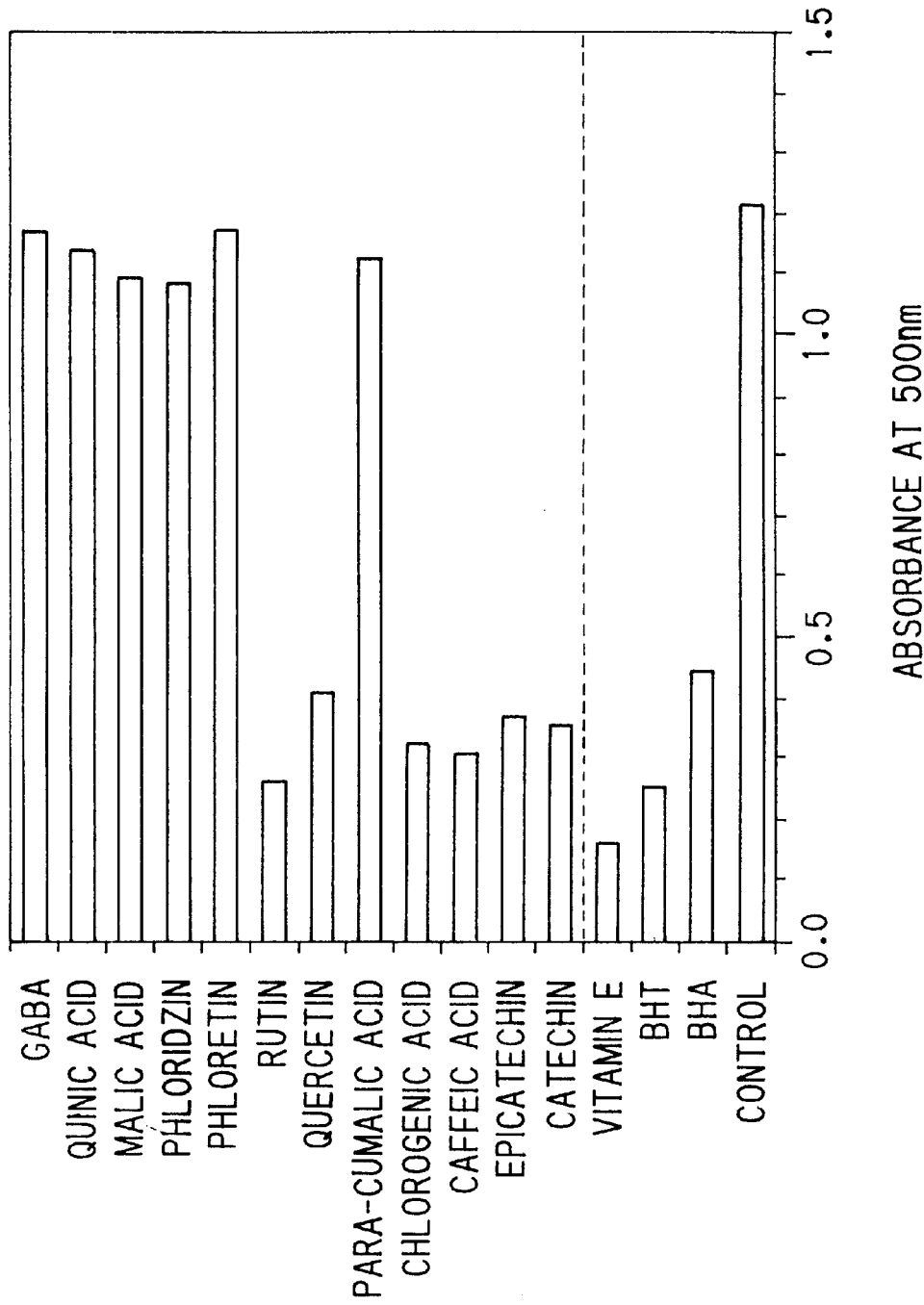
FIG. 4 is graphs showing the amounts of peroxylipids formed (the absorbances at 500 nm) in one week after various polyphenol compounds were added to respective reaction systems.

In FIG. 4, there are included, besides the above polyphenols, comparative substances, i.e. three known antioxidants (BHA, BHT and vitamine E) and typical compounds present in the above fractions A [quinic acid, malic acid and γ-aminobutyric acid (GABA)].

As a result, of the polyphenol compounds, six compounds [caffeic acid, chlorogenic acid, (+)-catechin, (−)-epicatechin, quercetin and rutin (quercetin-3-rha) had antioxidative activities equivalent to those of BHA and BHT. However, polyphenols such as p-coumaric acid, phloretin and phloridzin had no antioxidative activity. Further, no compounds present in the fractions A had any antioxidative activity.

By the comparison between (1) the amounts of the compounds present in apple and (2) their antioxidative activities, it could be judged that the high antioxidative activity exhibited by the unripe apple extract and the unripe apple juice is given mostly by chlorogenic acid, (+)-catechin and (−)-epicatechin.

From the above, it was confirmed that unripe apple "Fuji" had a high antioxidative activity. Further, the compounds showing said activity, present in the unripe apple "Fuji" were identified.

Successively, it was also investigated whether or not unripe apples other than unripe "Fuji" had the same antioxidative activity.

Figure 5:
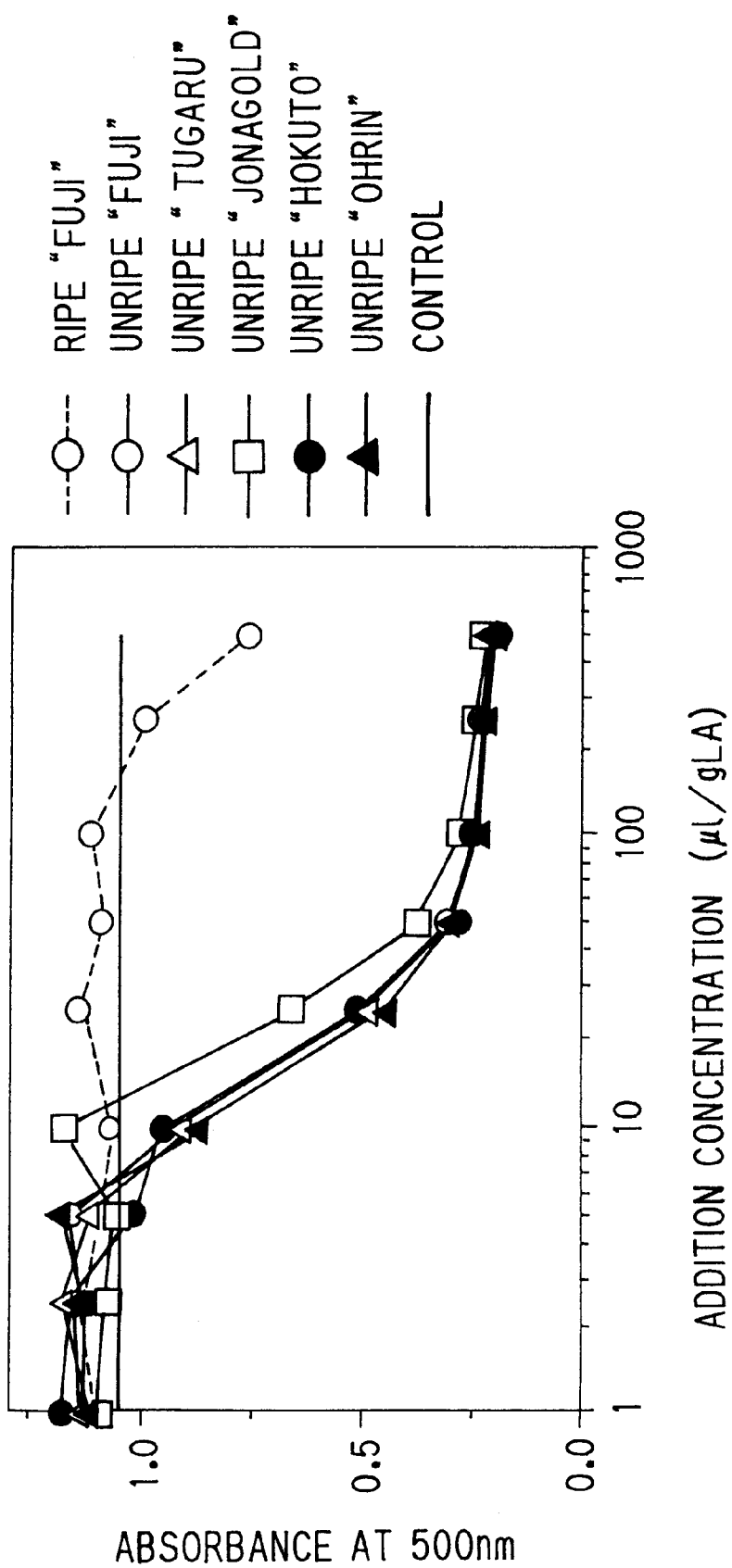
FIG. 5 is graphs each showing the relation between the amount of peroxylipid formed (the absorbance at 500 nm) and the addition concentration of polyphenol fraction of each unripe apple, in one week after said fraction was added to a reaction system.

From the extracts of various unripe apples ("Fuji", "Tugaru", "Jonagold", "Hokuto" and "Ohrin") were prepared respective fractions B (polyphenol fractions). Each fraction was added to a reaction system in a concentration range of 1–500 µl/g (linolic acid). One week after the addition, the amount of peroxylipid formed (absorbance at 500 nm) was measured. Its correlation with the concentration of fraction added is shown in FIG. 5. In FIG. 5, the result of unripe "Fuji" is also included for comparison.

As a result, each apple kind showed a high antioxidative activity and there was substantially no difference in antioxidative activity between apple kinds.

Further, the antioxidative activities of unripe fruits other than unripe apples were investigated.

Figure 6:
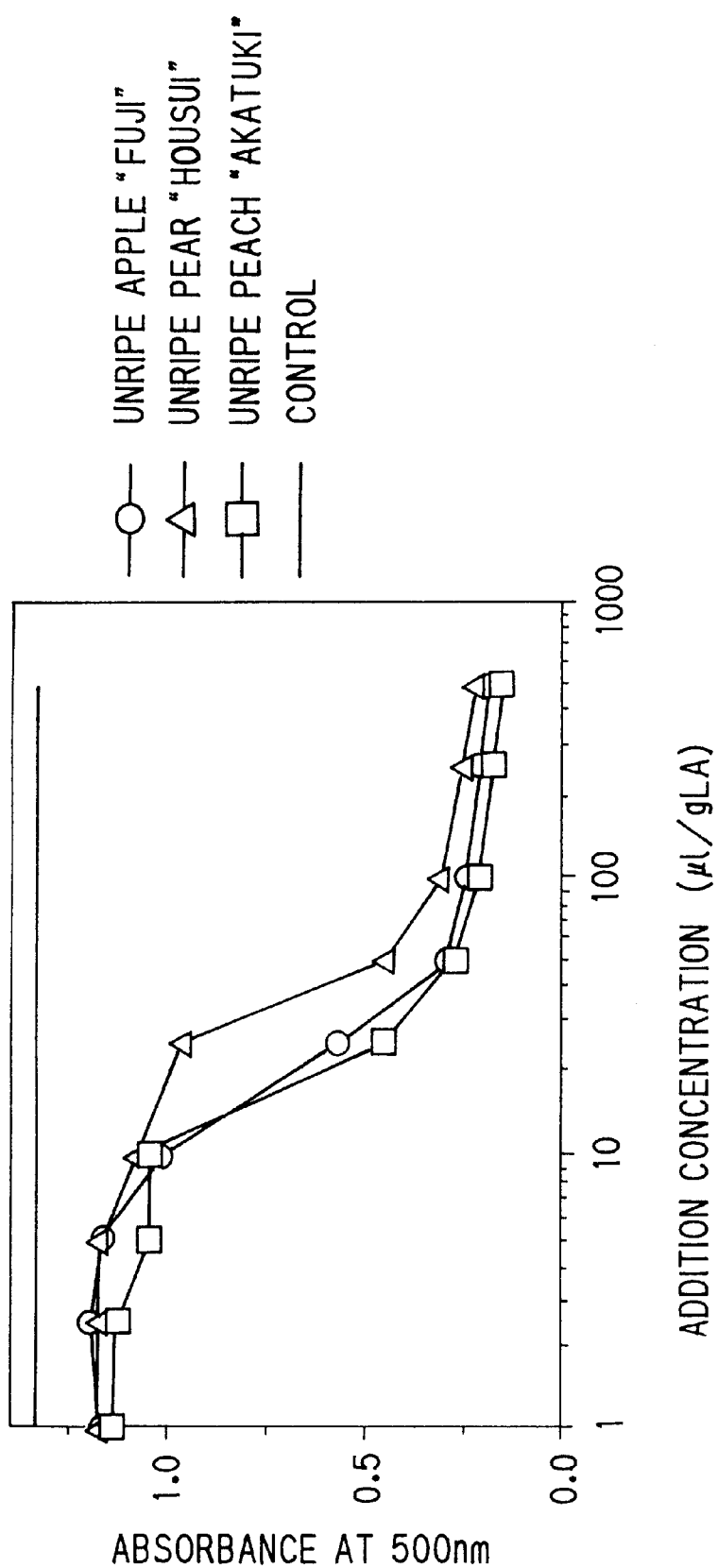
FIG. 6 is graphs each showing the relation between the amount of peroxylipid formed (the absorbance at 500 nm) and the addition concentration of polyphenol fraction of each unripe fruit, in one week after said fraction was added to a reaction system.

From the extracts of various unripe fruits (apple "Fuji", pear "Hohsui" and peach "Akatuki") were prepared respective fractions B (polyphenol fractions). Each fraction was added to a reaction system in a concentration range of 1–500 µl/g (linolic acid). One week after the addition, the amount of peroxylipid formed (absorbance at 500 nm) was measured. Its correlation with the concentration of fraction added is shown in FIG. 6.

As a result, the unripe peach had an antioxidative activity about equal to that of the unripe apple, and the unripe pear had a fairly high antioxidative activity although the activity was inferior to that of the unripe apple.

EXAMPLE 3

ACE (angiotensin I converting enzyme)-inhibiting activities of polyphenols present in unripe fruits
Starting materials: the following starting materials were used.
Unripe apples: the same as used in Example 2
Preparation of samples: "extract samples" and "polyphenol fractions" were prepared in the same manner as in Example 2.
Test method for ACE-inhibiting activity The test for ACE-inhibiting activity was conducted by an ordinary method.

That is, a sample solution was added to a commercial ACE solution to conduct preincubation; then, Bz-Gly-His-Leu was added as a substrate to give rise to a reaction; the His fragment formed by the reaction was labelled with orthophthaldialdehyde; and then the fluorescent intensity (Ex. 360 nm, Em. 490 nm) of the resulting solution was measured.

Figure 7:
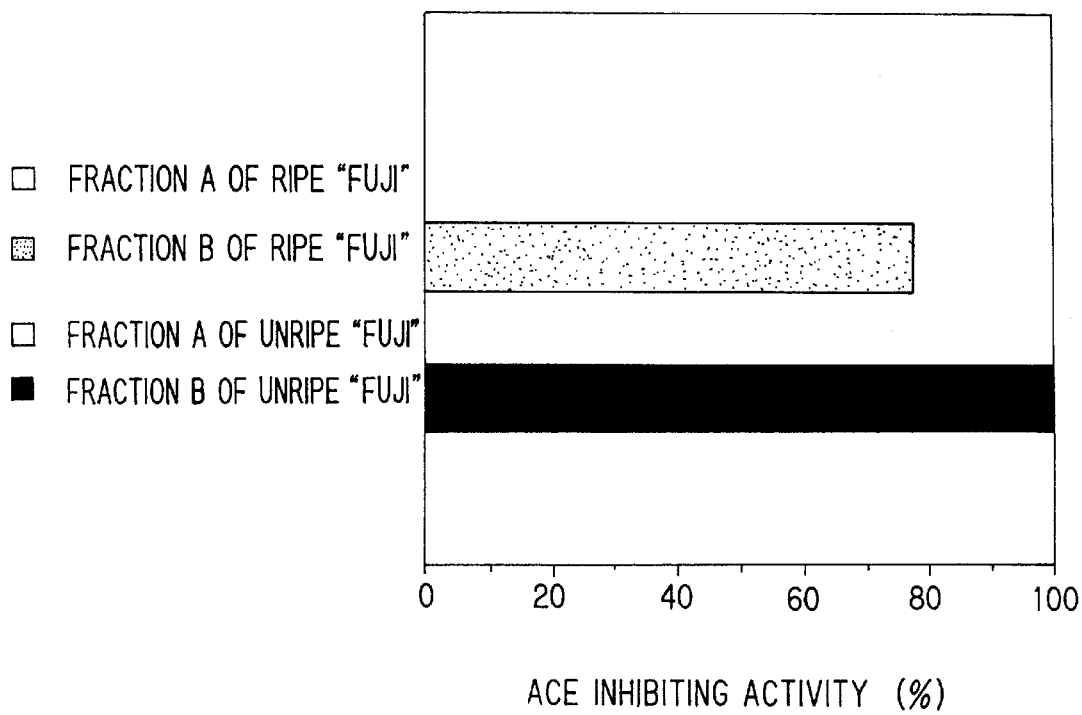
FIG. 7 is graphs each showing the angiotensin I converting enzyme (hereinafter referred to as ACE)-inhibiting activity of polyphenol fraction of unripe or ripe apple "Fuji".

The ACE-inhibiting activity of the sample solution was expressed by the following formula:

$$\{1-(S-S_B)/(C-C_B)\} \times 100 \ (\%)$$

where S: the fluorescent intensity of test solution,
C: the fluorescent intensity of comparative solution wherein water was used in place of the sample,
$S_B$: the fluorescent intensity of blank for S (the blank contained water in place of the enzyme), and
$C_B$: the fluorescent intensity of blank for C (the blank contained water in place of the enzyme).
Results of measurements Unripe apple "Fuji" extract and ripe apple "Fuji" extract were fractionated into respective unadsorbed fractions (fractions; A) and polyphenol fractions (fractions B), using Sep-pak C18. Each fraction was measured for ACE-inhibiting activity. The results are shown in FIG. 7.

Figure 8:
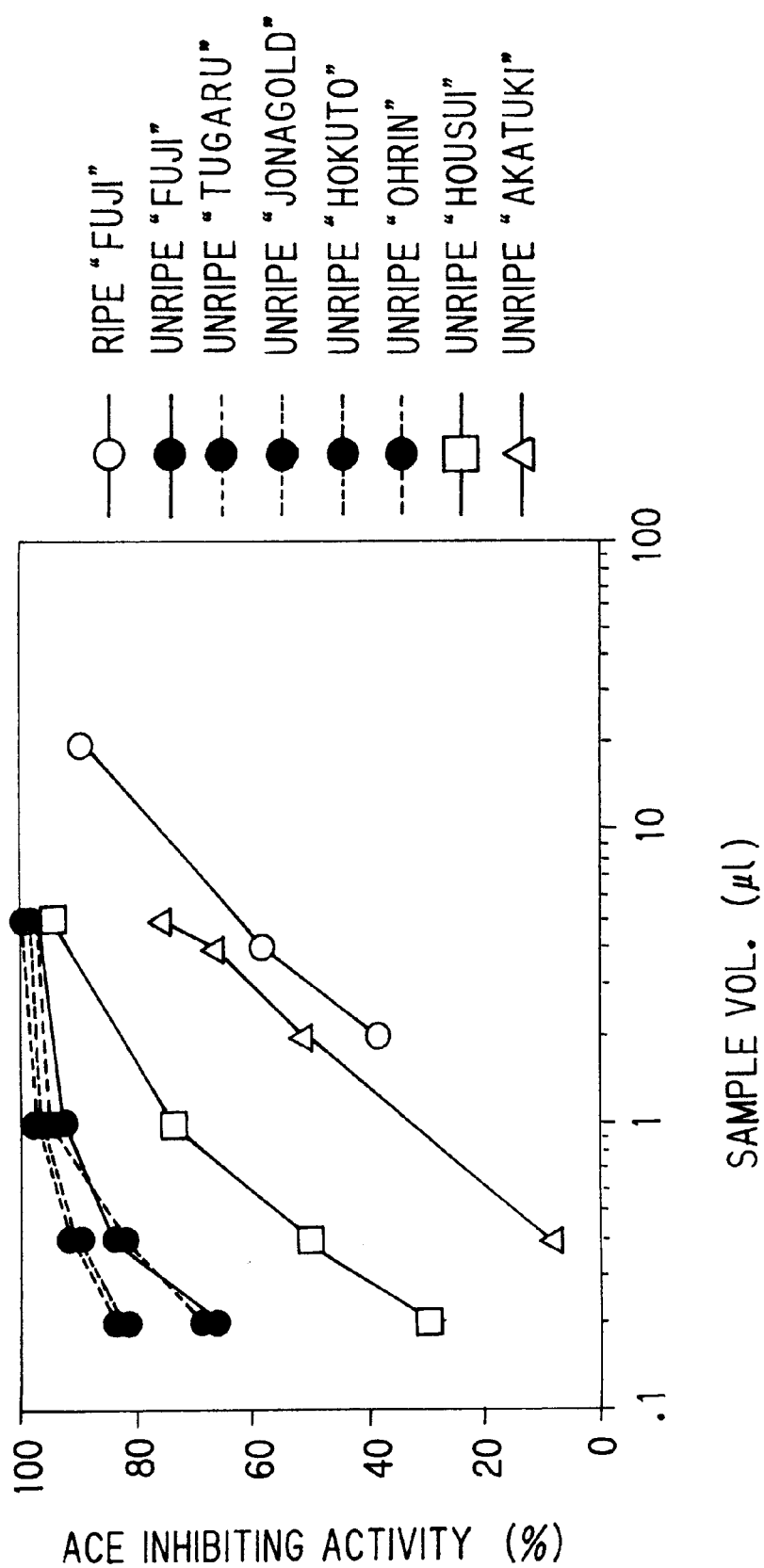
FIG. 8 is graphs showing the ACE-inhibiting activities of various polyphenol fractions B when each polyphenol fraction B was added to a reaction system in various amounts.

As a result, in both of the unripe and ripe apples, the fractions B showed high ACE-inhibiting activities. In particular, the fraction B of the unripe apple exhibitied 100% inhibition. In order to compare the ACE-inhibiting activities of the fractions B of the unripe and ripe apples in more detail, there were examined the changes of the ACE-inhibiting activities of the two fractions B when the amount of each fraction B added to the above reaction system was varied. The results are shown in FIG. 8.

As a result, the concentration showing 50% inhibition, i.e. $IC_{50}$ of the fraction B of the ripe apple was about 3 µl. In contrast, the $IC_{50}$ of the fraction B of the unripe apple was 0.1 µl or below. Thus, the fraction B of the unripe apple showed a very high ACE-inhibiting activity.

This high ACE-inhibiting activity of unripe apple was also observed in various apples other than "Fuji".

As seen from the above, unripe apples contain compounds having a high ACE-inhibiting activity, and the compounds are polyphenols. Incidentally, the ACE-inhibiting activities of unripe pear and unripe peach were lower than those of unripe apples.

Next, ACE-inhibiting activity was measured on each of simple polyphenols present in unripe apples and easily available as pure products. Specifically, there were examined the changes of the ACE-improving activities of such polyphenls when each polyphenol was added to a reaction system in various concentrations. The results are shown in FIG. 9.

Figure 9:
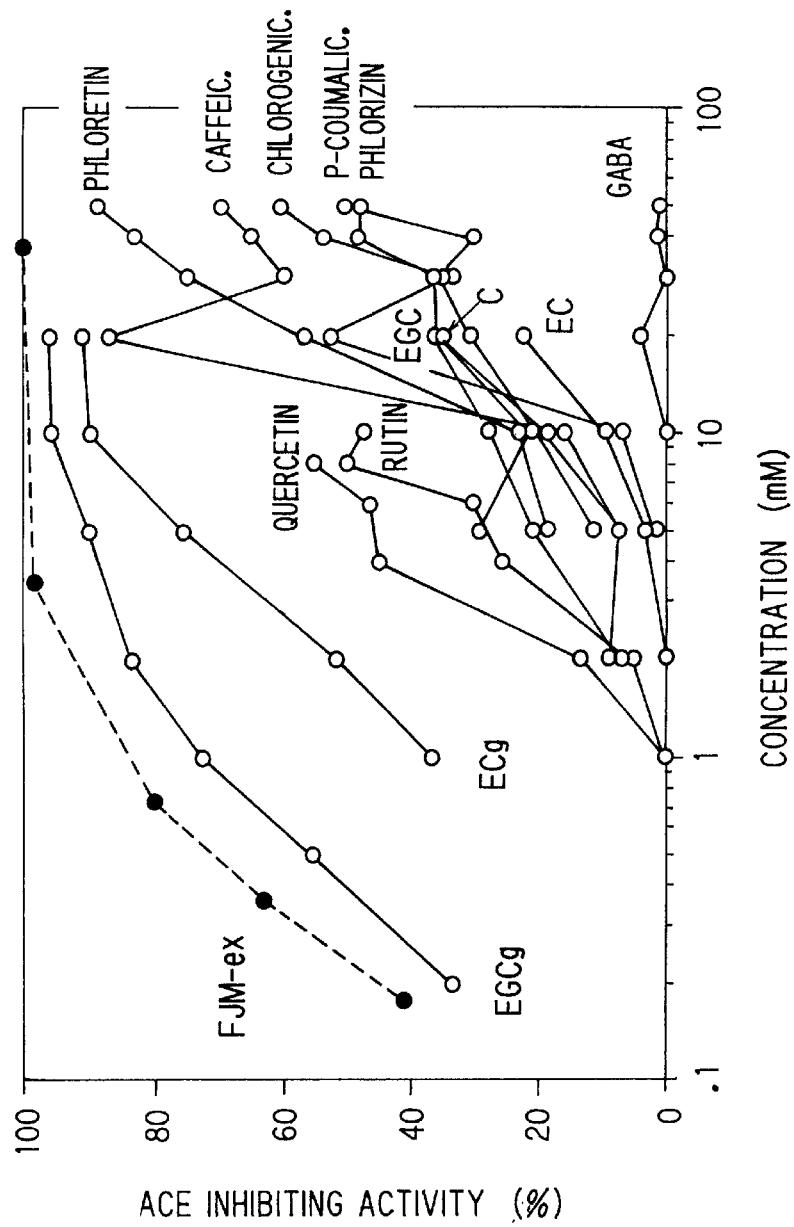
FIG. 9 is graphs showing the ACE-inhibiting activities of various polyphenol compounds when each polyphenol compound was added to a reaction system in various amounts.

FIG. 9 includes, for comparison, the ACE-inhibiting activities of tea catechins (tea catechins are known to have ACE-inhibiting activities). In FIG. 9, the $IC_{50}$ values of (−)-epigallocatechin gallate (EGCg) and (−)-epicatechin gallate (ECg) are 0.3 mM and 2 mM, respectively, and they have high ACE-inhibting activities. It is reported that GABALONG-tea (a trade name by Japanese tea marketer), in which the GABA concentration is increased by processing, showed a hypotensive activity in a test using SHRs (spontaneously hypertensive rats), but GABA showed no ACE-inhibiting activity in the present test.

Meanwhile, the polyphenols present in unripe apple showed ACE-inhibiting activities when they were at high concentrations. However, their $IC_{50}$ values were low and even in quercetin, which showed the highest activity, the $IC_{50}$ was as low as about 5 mM. Thus, the unripe apple polyphenols showed far-lower ACE-inhibiting activities than EGCg and ECg.

Hence, based on an assumption that all the polyphenols present in the fraction B of unripe apple are EGCg, the total polyphenol amount present in the fraction B was calculated using the calibration curve of EGCg. It was about 15,000 ppm and the polyphenol concentration in the fraction B was calculated to be 33.82 mM in terms of EGCg. Using this calculation value, the activity curve of the fraction B was plotted on FIG. 9, which indicated that the fraction B had a higher ACE-inhibiting activity ($IC_{50}$=0.2 mM) than EGCg. In actuality, the fraction B contains neither EGCg nor ECg and, as mentioned above, the simple polyphenols in unripe apple show no striking ACE-inhibiting activity. The high ACE-inhibiting activity of the unripe apple fraction B observed in FIG. 9 is thought to be owing to the co-presence of other unidentified polyphenols in the fraction B.

EXAMPLE 4

Identification of ACE-Inhibiting Compounds Present in Unripe Apple Polyphenols
Sample An unripe apple "Fuji" extract was obtained in the same manner as in Example 3, and the extract was subjected to solid-phase extraction to obtain a polyphenol fraction. This polyphenol fraction was used as a sample in the following.

Test method

A sample solution was fed into a Sephadex LH-20 column. The column was washed with distilled water. Then, elution was conducted with 20–60% methanol (acidificed with HCl) and 70% acetone (acidified with HCl) in this order to obtain polyphenol fractions.

The obtained polyphenol fractions were each subjected to compositional analysis by HPLC, measurement of total phenols and test for ACE-inhibiting activity. As necessary, there were also conducted measurement of absorption spectrum and gel permeation chromatography.

Test results

Fractionation by the use of Sephadex LH-20 column was tried in order to separate the ACE-inhibiting compounds in sample from other polyphenols. The fractions obtained by elution were subjected to compositional analysis of simple polyphenols by HLPC as well as to ACE-inhibiting test. All the simple polyphenols were eluted when 60% methanol as an elutant was passed through the column. Meanwhile, all the ACE-inhibiting compounds were present in the next elutant, i.e. 70% acetone.

The ACE-inhibiting compounds fraction obtained above was subjected to distillation to remove the solvent. The residue was freeze-dried to obtain ACE-inhibiting compounds as a powder. The compounds were readily soluble in water (the solution was orange) and the yield from 100 ml of the polyphenol fraction (fraction B) was about 0.7 g.

Figure 10:
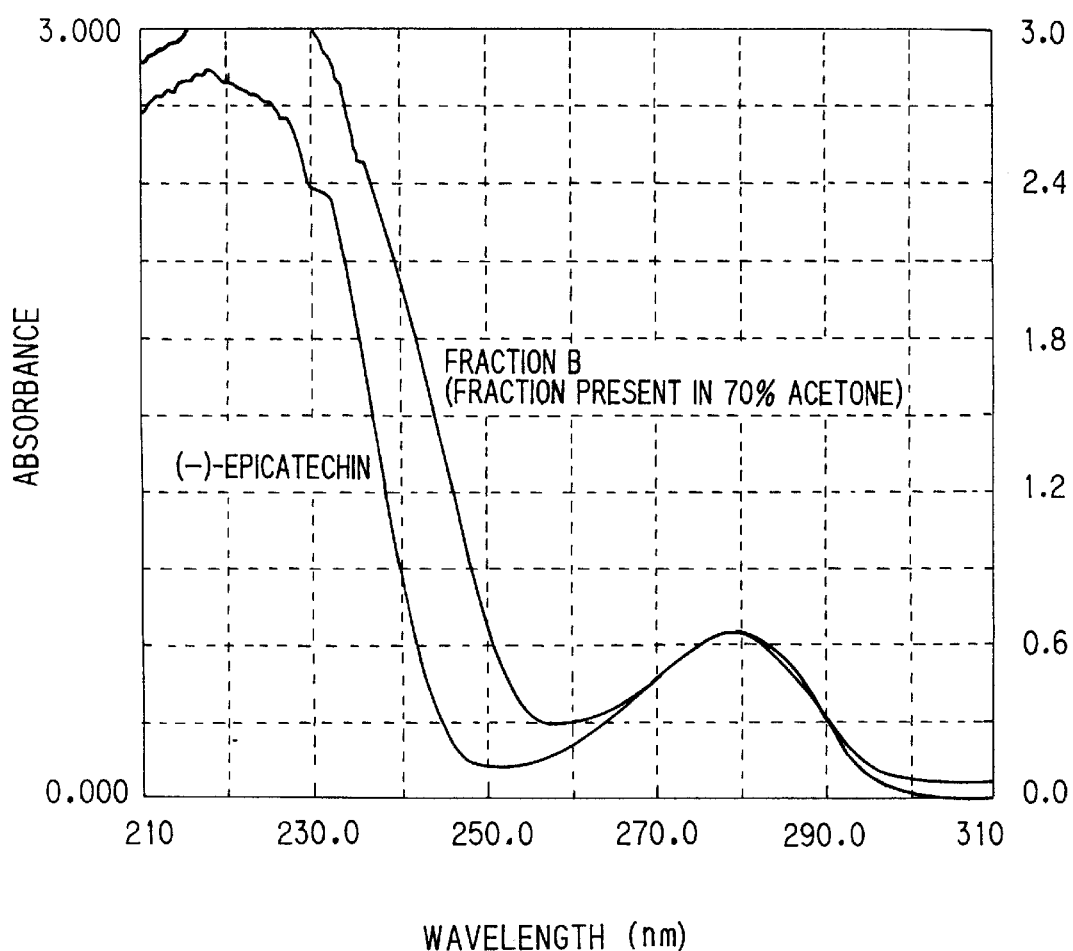
FIG. 10 is a graph showing the absorption spectrum of an isolated polyphenol fraction, measured by a spectrophotometer.

The above powder was dissolved in water and the solution was measured for absorption spectrum by spectrophotometer. The results are shown in FIG. 10.

The obtained spectrum showed a maximum absorption at 280 nm and had a shape similar to that of (+)-catechin or (−)-epicatechin. The above solution was subjected to an autoclvae treatment at 120° C. for 10 minutes. In the treatment, the solution turned red and anthocyanidin is thought to have been formed. These results strongly suggest that the above ACE-inhibiting compounds are procyanidins (regular polymers of catechins) known as condensed tannins. In view of the elution behavior in the Sephadex LH-20 column and the elution behavior in HPLC, said compounds are estimated to be not polymers of dimers or so (e.g. procyanidin $B_2$) but higher polymers.

Hence, the ACE-inhibiting compounds were subjected to molecular weight measurement by GPC. It is generally thought that the molecular weight measurement of polyphenol compounds by GFC (gel filtration chromatography) in an aqueous system (GFC in an aqueous system is generally used for proteins, etc.) is difficult because polyphenol compounds exhibit strong affinity with a filler in column, in the form of hydrophobic bond or hydrogen bond. Therefore, the phenolic hydroxyl group in each ACE-inhibiting compound was acetylated with pyridine/acetic anhydride so that each resulting material became soluble in organic solvents, and the resulting materials were subjected to GPC analysis in an organic solvent (THF). The results are shown in FIG. 11.

Figure 11:
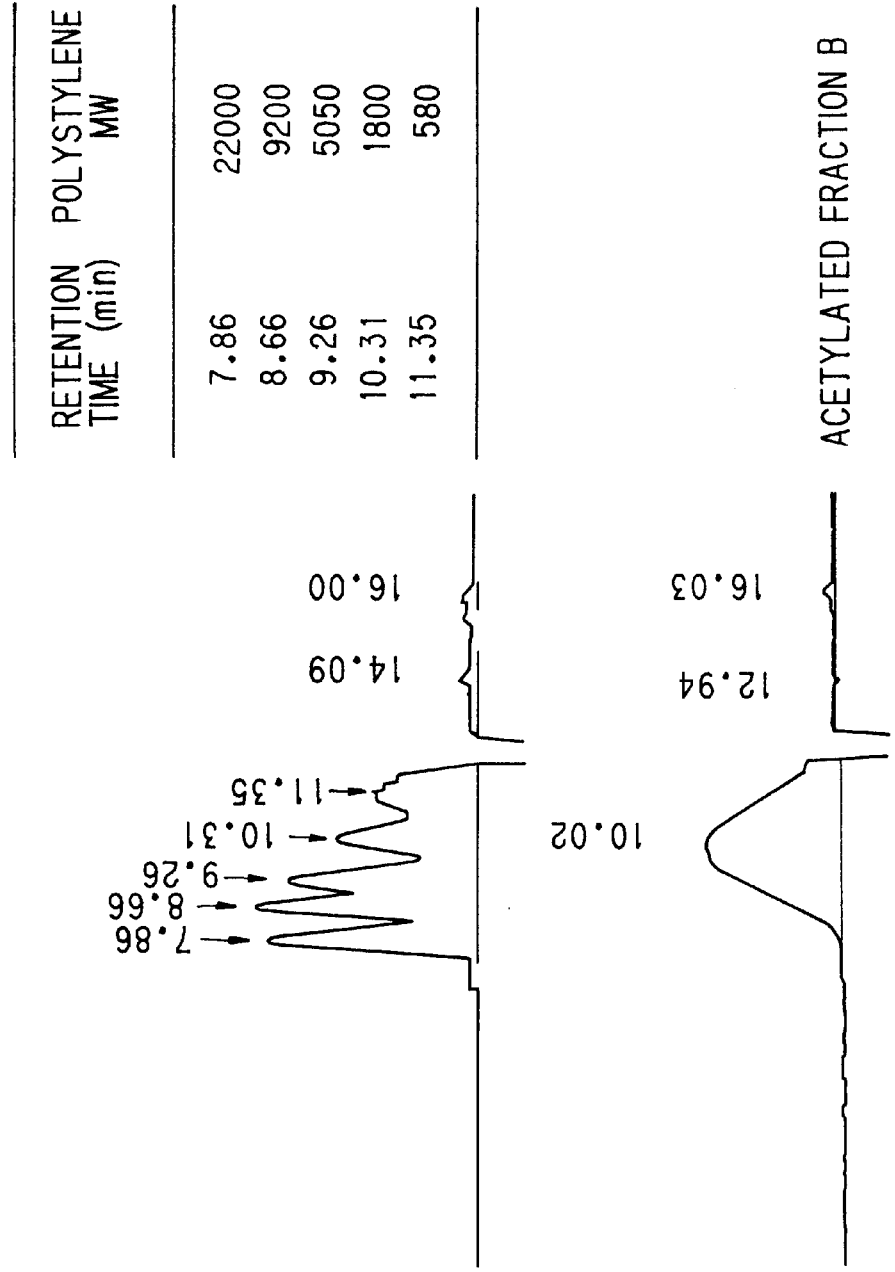
FIG. 11 is graphs showing the results of measurement by GPC, of molecular weights of condensed tannin.

In FIG. 11, a single broad peak appeared on the chromatogram. By using the molecular weight calibration curve simultaneously prepared using polystyrene, the average molecular weight of the ACE-inhibiting compounds was calculated to be about 2,000.

Figure 12:
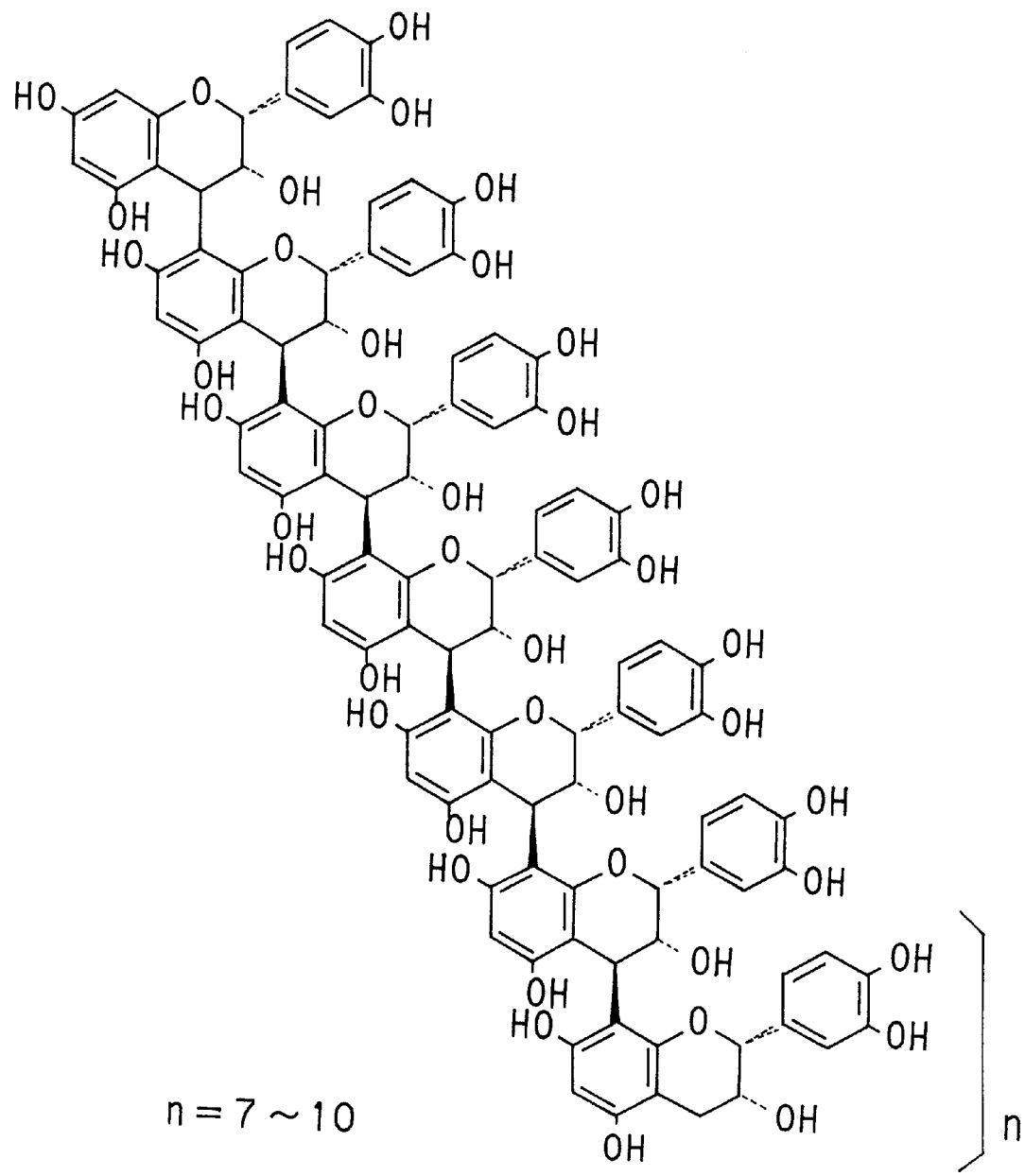
FIG. 12 is the structural formula of the ACE-inhibiting substance contained in the fruit polyphenol of the present invention.

The structural formula of the ACE-inhibiting compounds was tentatively estimated considering also the results of other tests not explained herein (e.g. partial decomposition using toluene-α-thiol, FAB-MS measurement), and is shown in FIG. 12.

From the above, the ACE-inhibiting compounds are judged to belong to condensed tannins.

The polyphenol fraction and the 70% acetone elute, i.e. the condensed tannins fraction obtained by subjecting the polyphenol fraction to Sephadex LH-20 fractionation were measured for amount of total phenols, and the two amounts were compared. The results are shown in Table 2.

TABLE 2

|  | Amount of total phenols (ppm in terms of catechin) | | |
| --- | --- | --- | --- |
|  | Before fractionation (Total polyphenols) | After fractionation (condensed tannins) | Before fractionation (%) After fractionation |
| Unripe apple extract | 22,800 | 10,800 | 47.3 |
| Ripe apple extract | 1,340 | 770 | 57.5 |

It is clear from Table 2 that the condensed tannins occupy about half of the total polyphenols present in unripe apple and are the components of largest amount present in said polyphenols.

The $IC_{50}$ of the condensed tannins to ACE was calculated, and it was very low (about 1/10 or below of that of EGCg on weight basis). Thus, the ACE-inhibiting compounds of the present invention had a very high ACE-inhibiting activity.

From the above results, it was judged that the unripe apple polyphenol can be used as an effective ACE-inhibiting agent.

EXAMPLE 5

Production of unripe fruit polyphenol

About 50 kg of unripe apples (5–10 g/apple) were crushed using a crusher while adding an appropriate amount of $SO_2$, and then pressed using an oil press. To the resulting juice was added about 50 ppm of a pectolysis enzyme,. and the mixture was subjected to centrifugation or filtration using diatomaceous earth and further to precision micro filtration to obtain 35 l of a clear juice. The clear juice was passed through a column filled with an industrial use synthetic adsorbent resin (6 l) of styrene-divinylbenzene type. Then, 6 l of 0.1% HCl-containing water was passed through the column to remove saccharide. Thereafter, 0.1% HCl-containing 50% ethanol was passed through to obtain 3 l of a fraction containing main polyphenols.

The fraction was concentrated under reduced pressure using an evaporator, to obtain 1.5 l of a concentrated fraction. The concentrated fraction was dried using a spray drier to obtain 228.2 g of an unripe apple polyphenol powder product.

The recovery (%) data are as follows.
Recovery in column: 95.6%
Recovery in spray drying: 93.0%
Recovery from juice: 0.65%
Powder recovery from polyphenols in juice: 88.9%

EXAMPLE 6

Antimutagenic activities of unripe fruit polyphenols

In this Example, antimutagenic activity was measured by modifying the ames method (Mutation Research, vol. 31, p. 347, 1975).

Starting materials and preparation of samples

The same as used in Examples 2, 3 and 4. The condensed tannins obtained in Example 4 are hereinafter referred to as "apple tannin".

Test method for antimutagenic activity

An antimutagenic compound [benzo(a)pyrene or Trp-P-2] solution was mixed with a phosphate buffer solution, a sample solution, S 9-mix and a salmonella (a solution obtained by culturing Salmonella typhimurium TA 98 or TA 100 overnight). The mixture was cultured at 37° C. for 2 days. The number of the resulting colonies was counted. The amount of each polyphenol used was shown based on a scale expressed in geometric progression, between 1 and 300 μg/plate. Antimutagenic activity was calculated using the following formula:

$$\text{antimutagenic activity } (\%) = \{(C-B)-(S-B)\} \div (C-B) \times 100$$

wherein S: number of colonies of test solution

C: number of colonies of control wherein water is used in place of the sample, and B: number of colonies of blank wherein water is used in place of the sample and the mutagenic compound.

Results

Figure 13:
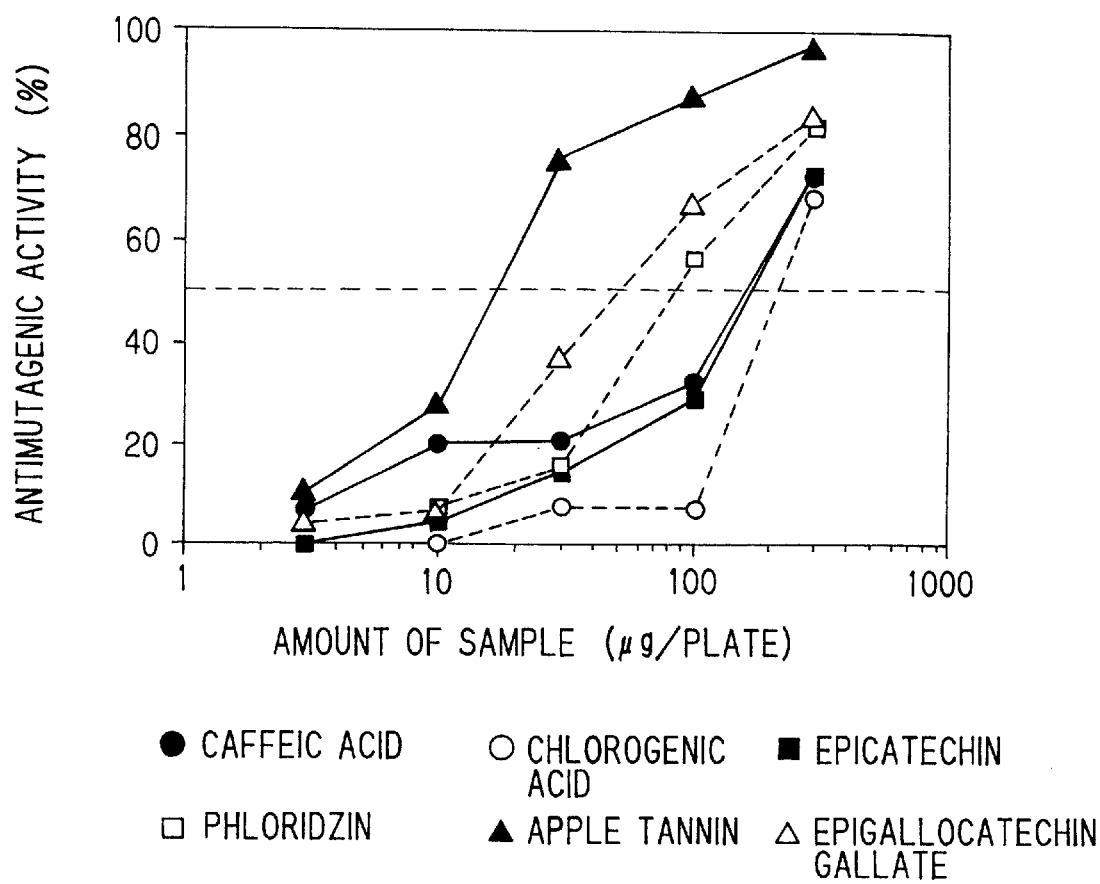
FIG. 13 is graphs showing the antimutagenic activities of various polyphenols to Trp-P-2.
Figure 14:
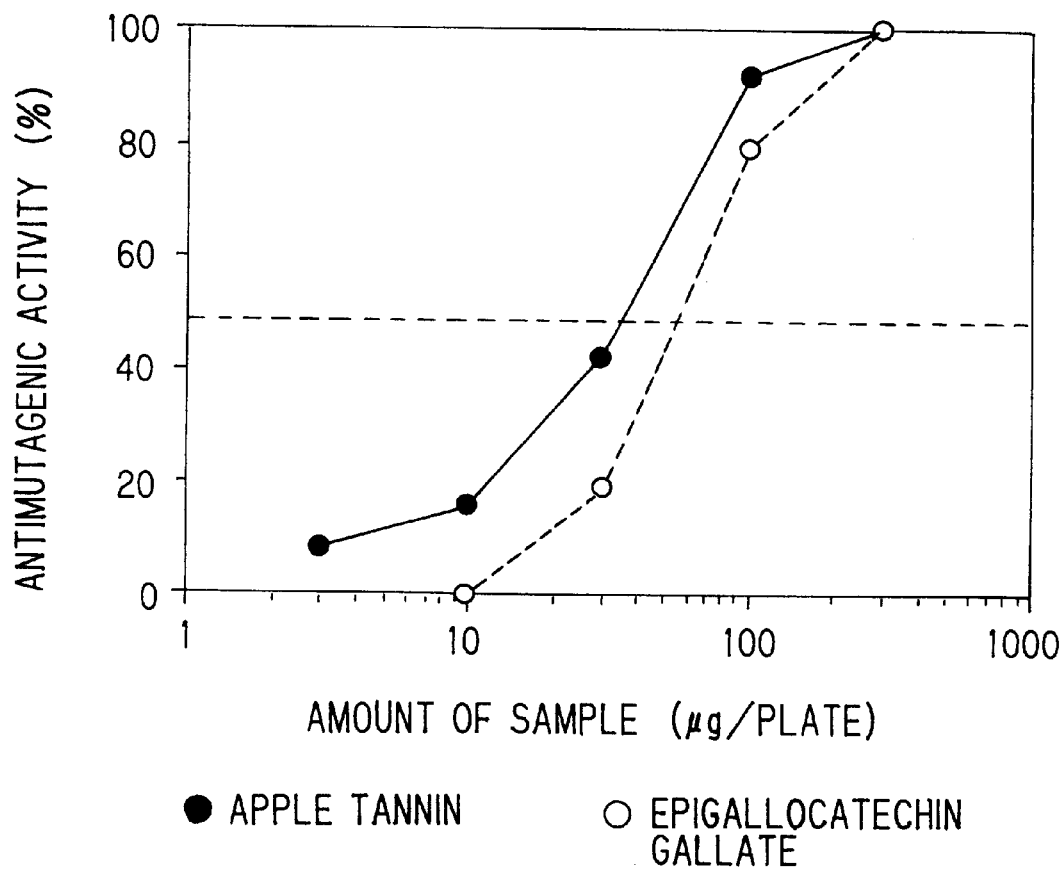
FIG. 14 is graphs showing the antimutagenic activities of apple tannin and epigallocatechin gallate to benzo[a]pyrene.

Of various polyphenols and apple tannin, their antimutagenic activites (%) to Trp-P-2 and benzo[a]pyrene are shown in FIG. 13 and FIG. 14, respectively. In each of FIGS. 13 and 14, the axis of ordinate shows antimutagenic activity (%), and the same antimutagenicity as shown in blank was taken as 100%. The axis of abscissa shows the amount of sample per plate.

As a result, apple tannin inhibited the mutagenicity of each mutagen dependently of the concentration of apple tannin, and its inhibition effect was equivalent to or even higher than that of epigallocatechin gallate. In the test of the present Example, apple tannin showed 50% antimutagenic activity to 1 μg of Trp-P-2, in an amount of about 17 μg (about 51 μg in the case of epigallocatechin gallate), and to 5 μg of benzo[a]pyrene in an amount of about 37 μg (about 56 μg in the case of epigallocatechin gallate). That is, apple tannin contained a large amount of compounds which strongly inhibitied the mutagenicity of mutagen (carcinogen). Thus, the fruit polyphenol obtained in the present invention is very effective also as an antimutagenic agent.

EXAMPLE 7

Hyaluronidase-inhibiting activities of polyphenols present in unripe fruits

In the present Example, hyaluronidase-inhibiting activity was measured to use it as an indicator for antiallergic activity.

Starting materials and preparation of samples

The same as used in Example 6.

Test method for hyaluronidase-inhibiting activity

Measurement of hyaluronidase-inhibiting activity was conducted based on a modification of the method described in J. Biol., vol. 250, p. 79, 1975. That is, a sample solution was added to a commercial hyaluronidase solution, and preincubation was conducted. Thereto was added a compound 48/80 (histamine releasant) solution, and hyaluronidase was activated at 37° C. Then, a hyaluronic acid solution was added as a substrate, and a reaction was allowed to take place.

The N-acetylglucosamine produced by the above reaction was subjected to the Elson-Morgan's procedure to develop a color. The color was measured for absorbance at 586 nm. Hyaluronidase-inhibiting activity (%) was calculated using the following formula:

$$\text{hyaluronidase-inhibiting activity } (\%) = \{(C-C_B)-(S-S_B)\} \div (C-C_B) \times 100$$

wherein S: absorbance of test solution,

C: absorbance of control wherein a buffer solution is used in place of the sample, $S_B$: absorbance of blank for S (the blank contained no enzyme), and $C_B$: absorbance of blank for C (the blank contained no sample and no enzyme).

Results

Figure 15:
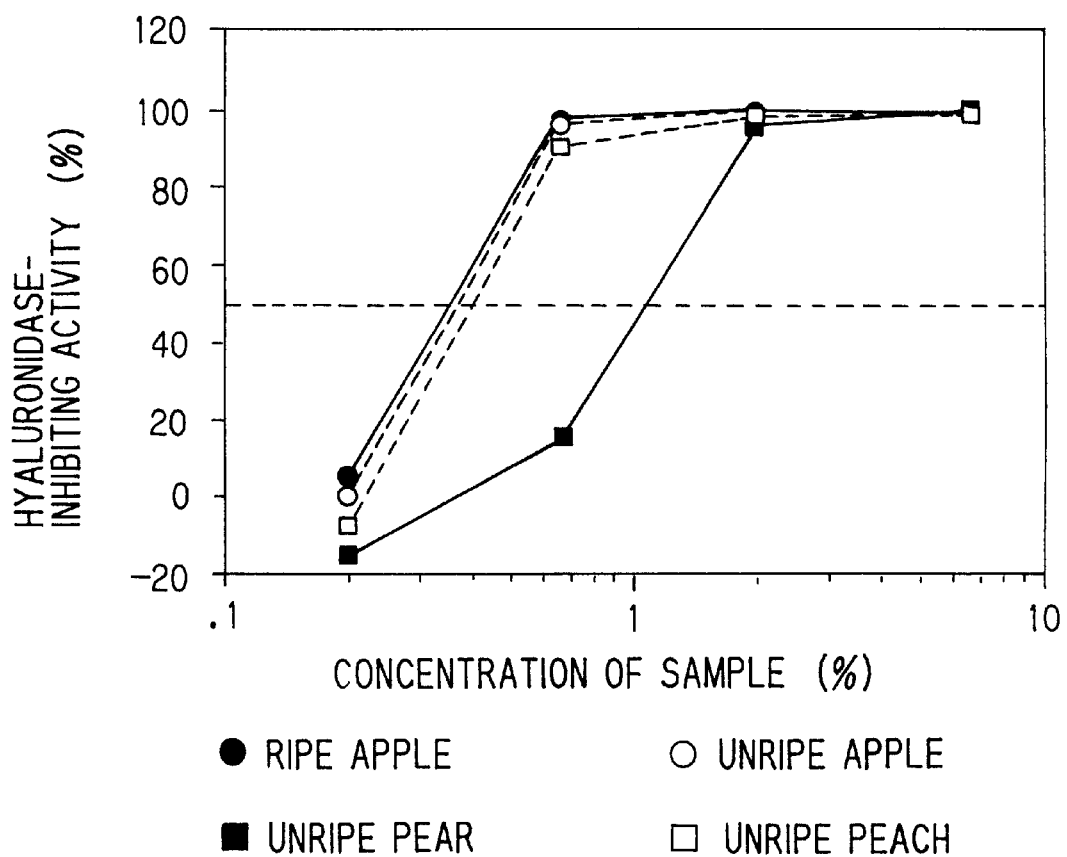
FIG. 15 is graphs showing the hyaluronidase-inhibiting activities of various fruit extracts.
Figure 16:
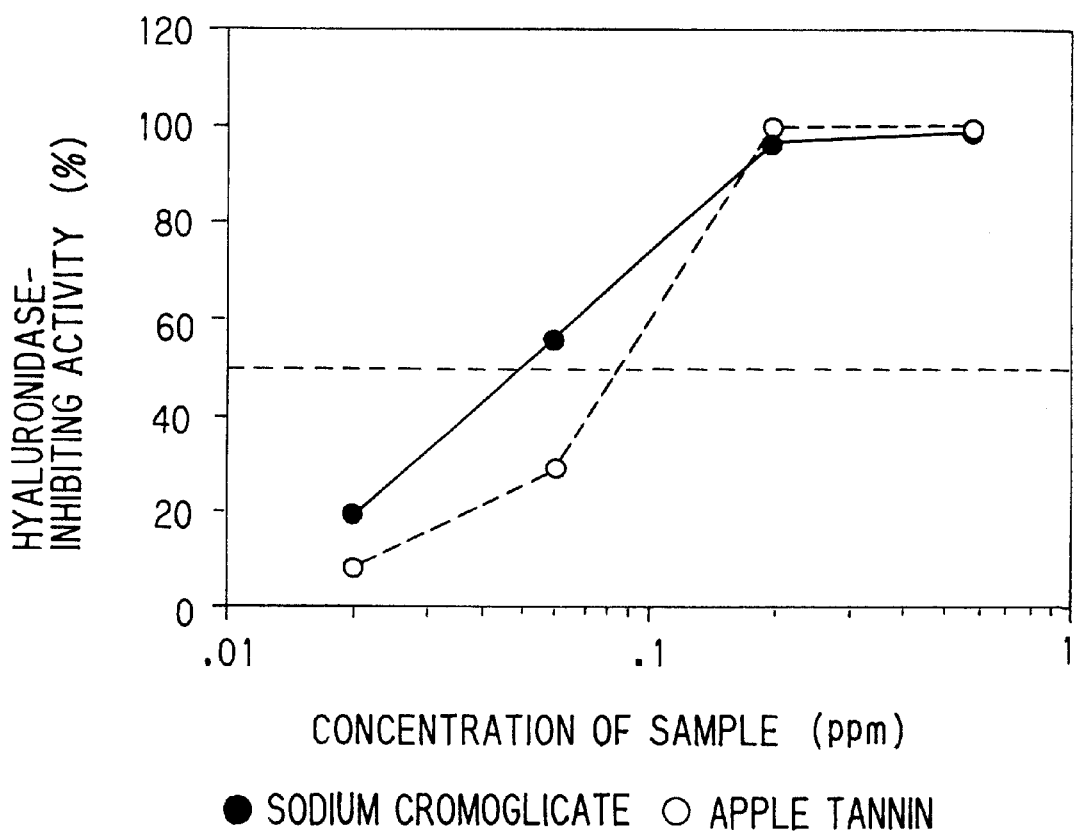
FIG. 16 is graphs showing the hyaluronidase-inhibiting activities of an antiallergic agent (sodium cromoglicate) and apple tannin.

The hyaluronidase-inhibiting activities of various fruit extracts are shown in FIG. 15, and the hyaluronidase-inhibiting activities of sodium cromoglicate and apple tannin are shown in FIG. 16.

As a result, each fruit extract and apple tannin showed hyaluronidase-inhibiting activities dependently of their concentrations. In FIG. 16, the hyaluronidase-inhibiting activity of sodium cromoglicate is shown for comparison. The $IC_{50}$ (the concentration at which 50% inhibition is exhibited) of sodium cromoglicate was about 0.051 mg/ml while the $IC_{50}$ of apple tannin was about 0.086 mg/ml and close to that of sodium cromoglicate.

Thus, this polyphenol (apple tannin) contained a large amount of compounds inhibiting the activity of hyaluronidase (an enzyme associated with I type allergy). Therefore, the fruit polyphenol obtained in the present invention is very effective also as an antiallergic agent.

EXAMPLE 8

Glucosyltransferase-inhibiting activities of polyphenols present in unripe fruits In the present Example were investigated the inhibitory activities of fruit polyphenols to GTase [this enzyme forms insoluble glucan from sucrose and is produced by *S. sobrinus* (a typical cariogenic bacteria].

Starting materials and preparation of samples

The same as used in Examples 6 and 7.

Bacterium used: *Streptococcus sobrinus* ATCC 33478

Preparation of GTase

GTase of *S. sobrinus* was prepared as follows.

*S. sobrinus* was cultured in a TTY medium [Agric. Biol. Chem., 54 (11), pp. 2925–2929, 1990] at 37° C. for 18 hours. Centrifugation was conducted to remove bacterial cells and obtain a supernatant. To the supernatant was added ammonium sulfate to 50% saturation. Then, centrifugation was conducted to recover the resulting precipitate. The precipitate was redissolved in a 0.05 M phosphate buffer solution (pH 6.5). The resulting solution was dialyzed with the same buffer solution. The GTase in the dialyzate was purified and removed by hydroxyapatite chromatography. The GTase (capable of forming insoluble glucan) was eluted with an about 0.4 M phosphate buffer solution. The GTase-containing elute was used for the following test.

Test method for GTase-inhibiting activity

A purified GTase solution and a sample solution were added to 1 ml of a substrate solution [a 0.1 M phosphate buffer solution (pH 6.5) containing 2% of sucrose, 0.1% of sodium azide and 40 μM of dextran T10]. Water was added for dilution to make the total volume 2 ml. The resulting solution was subjected to a reaction at 37° C. for 18 hours. The amount of insoluble glucan formed by the reaction was measured as a turbidity expressed by an absorbance at 550 nm, and the formation ratio (%) of insoluble glucan was calculated using the following formula:

formation ratio (%) of insoluble glucan=$(SS-SB)\div(CS-CB)\times100$ wherein SS: absorbance of sample, SB: absorbance of blank for sample (the blank contained no enzyme), CS: absorbance of control (containing no sample), and CB: absorbance of blank for control (the blank contained no sample and no enzyme).

Results

Figure 17:
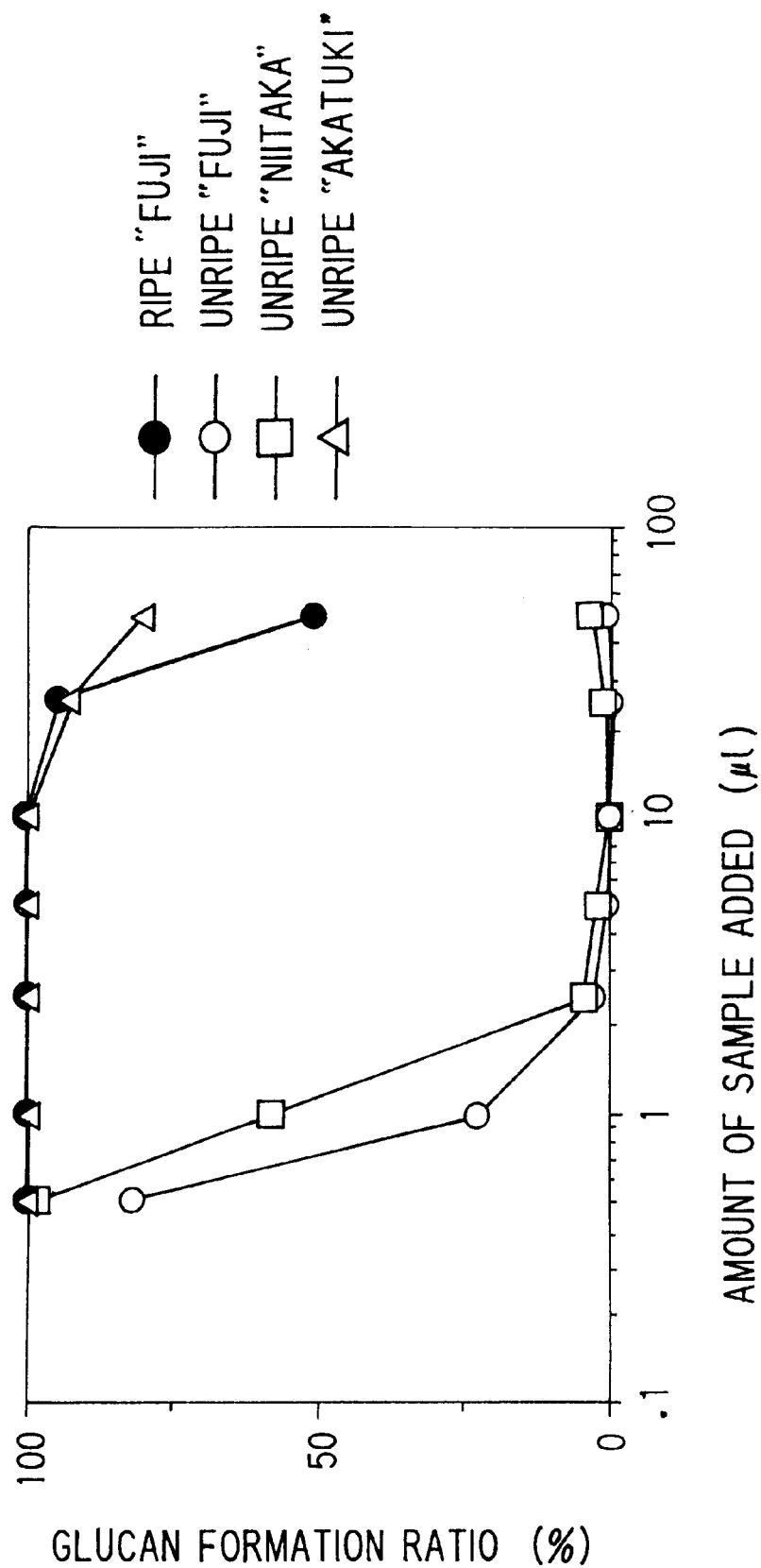
FIG. 17 is graphs showing the relations between the amount of insoluble glucan formed and the amount of fruit polyphenol fraction added, when various fruit polyphenol fractions were added to respective reaction systems.
Figure 18:
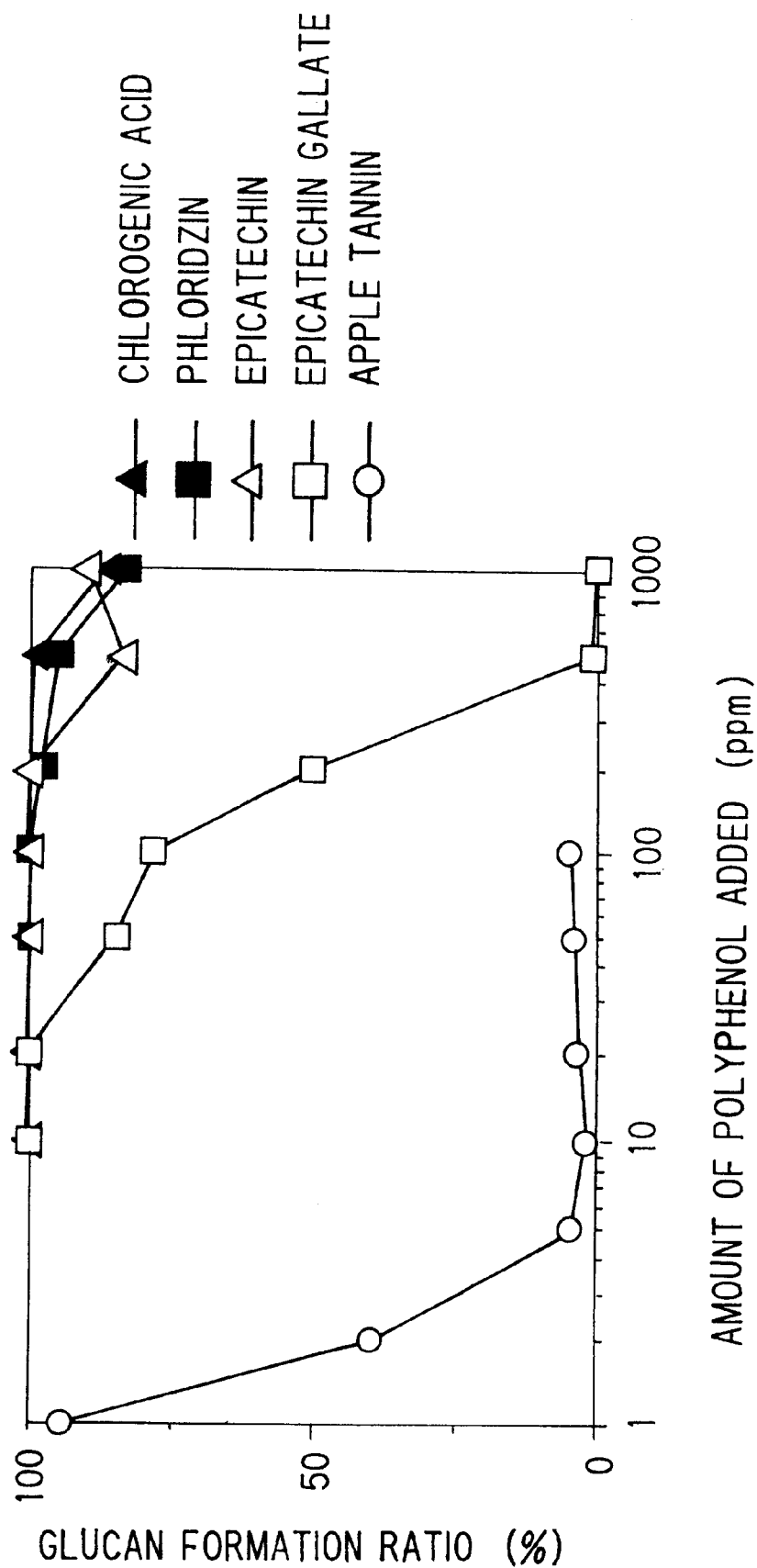
FIG. 18 is graphs showing the relations between the amount of insoluble glucan formed and the amount of polyphenol compound added, when various polyphenol compounds were added to respective reaction systems.

The GTase-inhibiting activities of the polyphenol fractions of various fruit extracts are shown in FIG. 17, and the GTase-inhibiting activities of individual polyphenol compounds are shown in FIG. 18. In each of FIGS. 17 and 18, the axis of ordinate indicates the formation ratio (%) of insoluble glucan, and the formation ratio (%) in control (containing no sample) was taken as 100%. The axis of abscissa indicates the amount (volume or concentration) of sample or polyphenol added to reaction system.

As shown in FIG. 17, of the polyphenol fractions of various fruit extracts, particularly the polyphenol fractions of unripe apple "Fuji" and unripe pear "Niitaka" showed striking GTase-inhibiting activities. The $IC_{50}$ of ripe apple "Fuji" to GTase was about 50 μl while the $IC_{50}$ of unripe apple "Fuji" to GTase was about 0.7 μl. Thus, the unripe apple had a GTase-inhibiting activity about 70 times higher than ripe apple.

Next, there were investigated the GTase-inhibiting activities of various polyphenol compounds including those present in apple. As shown in FIG. 18, of the polyphenol compounds present in apple, chlorogenic acid and phloridzin each had a very low GTase-inhibiting activity. Meanwhile, of the catechins, epicatechin monomer had a very low GTase-inhibiting activity but high-molecular epicatechin polymers (indicated as apple tannin in FIG. 18) represented by the estimated structural formula of FIG. 12 had a high GTase-inhibiting activity. In FIG. 18 is also shown the result of epicatechin gallate (a typical catechin present in green tea and known as a GTase-inhibiting substance) [Agric. Biol. Chem., 5 (11), pp. 2925–2929, 1990; Chem. Pharm. Bull., 38 (39), pp. 717–720, 1990]. From the calculation made using FIG. 18, the $IC_{50}$ of epicatechin gallate to GTase was about 200 ppm while that of apple tannin was about 2 ppm. Thus, apple tannin had a GTase-inhibiting activity about 100 times higher than epicatechin gallate. From these results, the high GTase-inhibiting activity of unripe apple "Fuji" seen in FIG. 17 is thought to be owing to the presence of apple tannin.

Thus, the fruit polyphenol obtained in the present invention contains compounds of high GTase-inhibiting activity and accordingly is very effective also as an anticariogenic agent.

What is claimed is:

1. A mixture consisting essentially of polyphenols obtained by pressing or extraction of unripe Rosaceae fruits to form a juice or extract, treating the juice or extract with an absorbent which selectively adsorbs the polyphenols contained in the juice or extract, eluting the polyphenols from the adsorbent with ethyl alcohol, and recovering the mixture of polyphenols from the eluate; the mixture of polyphenols consisting essentially of caffeic acid, caffeic acid esters, p-coumaric acid, p-coumaric acid esters, phloretin, phloretin glycosides, quercetin, quercetin glycosides, catechin, epicatechin, and condensed tannins.

2. A mixture of polyphenols according to claim 1, wherein the unripe Rosaceae fruits are apples, pears or peaches.

3. A mixture of polyphenols according to claim 1, wherein the mixture of polyphenols is recovered from the eluate by spray-drying.

4. A mixture of polyphenols according to claim 1, wherein the mixture of polyphenols is recovered from the eluate by freeze-drying.

5. The mixture of claim 1 wherein the Rosaceae fruit used to form the juice or extract are unripe apples and the phenolic components of the mixture, catechin and epicatechin, are expressed in an HPLC chromatogram as sharp peaks at 280 nm at a retention time between 4 and 20 minutes as shown in FIG. 1.

6. The mixture of claim 1 wherein the Rosaceae fruit used to form the juice or extract are unripe apples and the phenolic component of the mixture, caffeic acid, is expressed in an HPLC chromatogram as a sharp peak at 325 nm at a retention time between 10 and 20 minutes as shown in FIG. 1.

7. The mixture of claim 1 wherein the Rosaceae fruit used to form the juice or extract are unripe apples and the phenolic component, quercetin glycoside, is expressed in an HPLC chromatogram as several small peaks at 350 nm at a retention time between 30 and 70 minutes as shown in FIG. 1.

* * * * *